United States Patent
Gurtner et al.

(10) Patent No.: US 8,063,263 B2
(45) Date of Patent: Nov. 22, 2011

(54) METHODS FOR THE TREATMENT OR PREVENTION OF SCARS AND/OR KELOIDS

(75) Inventors: Geoffrey C. Gurtner, Palo Alto, CA (US); Reinhold H. Dauskardt, Menlo Park, CA (US); Michael T. Longaker, Atherton, CA (US); Paul Yock, Atherton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 270 days.

(21) Appl. No.: 12/358,159

(22) Filed: Jan. 22, 2009

(65) Prior Publication Data

US 2009/0163844 A1    Jun. 25, 2009

Related U.S. Application Data

(63) Continuation of application No. 11/888,978, filed on Aug. 3, 2007, now Pat. No. 7,683,234.

(60) Provisional application No. 60/835,654, filed on Aug. 3, 2006.

(51) Int. Cl.
| | |
|---|---|
| *A61F 13/00* | (2006.01) |
| *A61B 17/00* | (2006.01) |
| *A61B 17/08* | (2006.01) |
| *C08L 15/00* | (2006.01) |

(52) U.S. Cl. ............... 602/41; 602/42; 602/43; 602/50; 602/53; 602/54; 606/201; 606/216; 523/111

(58) Field of Classification Search ............. 602/41–59; 128/888–889; 424/443–449; 606/213–216; 523/105, 111, 122
See application file for complete search history.

(56) References Cited

U.S. PATENT DOCUMENTS

| | | | |
|---|---|---|---|
| 114,750 | A | 5/1871 | Battersby |
| 363,538 | A | 5/1887 | Penny |
| 1,074,413 | A | 9/1913 | De Baun et al. |
| 1,774,489 | A | 8/1930 | Sarason |
| 1,969,188 | A | 8/1934 | Spicer |
| 2,018,517 | A | 10/1935 | Fetter |
| 2,303,131 | A | 11/1942 | Morgan |
| 2,371,978 | A | 3/1945 | Perham |

(Continued)

FOREIGN PATENT DOCUMENTS

RU    2 019 138 C1    9/1994

(Continued)

OTHER PUBLICATIONS

3M Healthcare. (Date Unknown). "3M™ Steri-Strip™ S Surgical Skin Closure," 3M HealthCare: St. Paul, MN, one page.

(Continued)

*Primary Examiner* — Patricia Bianco
*Assistant Examiner* — Ophelia Hawthorne
(74) *Attorney, Agent, or Firm* — Morrison & Foerster LLP

(57) ABSTRACT

Devices, bandages, kits and methods are described that can control or regulate the mechanical environment of a wound to ameliorate scar and/or keloid formation. The mechanical environment of a wound includes stress, strain, and any combination of stress and strain. The control of a wound's mechanical environment can be active, passive, dynamic, or static. The devices are configured to be removably secured to a skin surface in proximity to the wound site and shield the wound from endogenous and/or exogenous stress.

39 Claims, 16 Drawing Sheets

U.S. PATENT DOCUMENTS

| | | | |
|---|---|---|---|
| 2,722,220 | A | 11/1955 | Mestrand |
| 3,103,218 | A | 9/1963 | Ajemian |
| 3,402,716 | A | 9/1968 | Baxter |
| 3,487,836 | A | 1/1970 | Niebel et al. |
| 3,528,426 | A | 9/1970 | Vukojevic |
| 3,575,782 | A | 4/1971 | Hansen |
| 3,645,835 | A | 2/1972 | Hodgson |
| 3,698,395 | A | 10/1972 | Hasson |
| 3,863,640 | A | 2/1975 | Haverstock |
| 3,926,193 | A | 12/1975 | Hasson |
| 3,933,158 | A | 1/1976 | Haverstock |
| 3,983,878 | A | 10/1976 | Kawchitch |
| 4,038,989 | A | 8/1977 | Romero-Sierra et al. |
| 4,073,298 | A | 2/1978 | Le Roy |
| 4,114,624 | A | 9/1978 | Haverstock |
| 4,141,363 | A | 2/1979 | James et al. |
| 4,173,131 | A | 11/1979 | Pendergrass et al. |
| 4,222,383 | A | 9/1980 | Schossow |
| 4,282,005 | A | 8/1981 | Sato et al. |
| 4,370,981 | A | 2/1983 | Sanderson |
| 4,423,731 | A | 1/1984 | Roomi |
| 4,496,535 | A | 1/1985 | Gould et al. |
| 4,531,521 | A | 7/1985 | Haverstock |
| 4,539,990 | A | 9/1985 | Stivala |
| 4,605,005 | A | 8/1986 | Sheehan |
| 4,696,301 | A | 9/1987 | Barabe |
| 4,699,133 | A | 10/1987 | Schäfer et al. |
| 4,702,251 | A | 10/1987 | Sheehan |
| 4,742,826 | A | 5/1988 | McLorg |
| 4,780,168 | A | 10/1988 | Beisang et al. |
| 4,787,381 | A | 11/1988 | Hubbard et al. |
| 4,815,468 | A | 3/1989 | Annand |
| 4,825,866 | A | 5/1989 | Pierce |
| 4,950,282 | A | 8/1990 | Beisang et al. |
| 4,984,584 | A | 1/1991 | Hansen et al. |
| 5,011,492 | A | 4/1991 | Heimerl et al. |
| 5,047,047 | A | 9/1991 | Yoon |
| 5,058,579 | A | 10/1991 | Terry et al. |
| 5,066,299 | A | 11/1991 | Bellingham |
| 5,176,703 | A | 1/1993 | Peterson |
| 5,259,835 | A | 11/1993 | Clark et al. |
| 5,549,713 | A * | 8/1996 | Kim ............................ 606/131 |
| 5,552,162 | A | 9/1996 | Lee |
| 5,562,705 | A | 10/1996 | Whiteford |
| 5,662,624 | A | 9/1997 | Sundström et al. |
| 5,662,714 | A * | 9/1997 | Charvin et al. ............ 623/15.12 |
| 5,758,662 | A | 6/1998 | Hall |
| 5,759,560 | A | 6/1998 | Dillon |
| 5,779,659 | A | 7/1998 | Allen |
| 5,891,076 | A | 4/1999 | Fabo |
| 6,007,564 | A | 12/1999 | Haverstock |
| 6,284,941 | B1 | 9/2001 | Cox et al. |
| 6,410,818 | B1 | 6/2002 | Oyaski |
| 6,469,066 | B1 | 10/2002 | Dosch et al. |
| 6,573,419 | B2 | 6/2003 | Naimer |
| 6,759,481 | B2 | 7/2004 | Tong |
| 6,822,133 | B2 | 11/2004 | Lebner |
| 6,831,205 | B2 | 12/2004 | Lebner |
| 6,870,074 | B2 | 3/2005 | Gilman |
| 6,986,855 | B1 | 1/2006 | Hood et al. |
| 7,066,934 | B2 | 6/2006 | Kirsch |
| 7,332,641 | B2 | 2/2008 | Lebner et al. |
| 7,354,446 | B2 | 4/2008 | Lebner |
| 7,414,168 | B2 | 8/2008 | Lebner |
| 7,511,185 | B2 | 3/2009 | Lebner |
| 7,563,941 | B2 | 7/2009 | Lebner et al. |
| 2002/0013300 | A1 | 1/2002 | Capelli-Schellpfeffer |
| 2003/0220700 | A1 | 11/2003 | Hammer et al. |
| 2005/0070956 | A1 | 3/2005 | Rousseau |
| 2005/0095276 | A1 | 5/2005 | Kartheus et al. |
| 2005/0125051 | A1 | 6/2005 | Eidenschink et al. |
| 2006/0009099 | A1 | 1/2006 | Jonn et al. |
| 2006/0037091 | A1 | 2/2006 | Gurtner et al. |
| 2006/0246802 | A1 | 11/2006 | Hughes et al. |
| 2007/0093161 | A1 | 4/2007 | Eede et al. |
| 2008/0033334 | A1 | 2/2008 | Gurtner et al. |
| 2008/0051687 | A1 | 2/2008 | Rogers |
| 2009/0131845 | A1 | 5/2009 | Gurtner et al. |
| 2009/0131846 | A1 | 5/2009 | Gurtner et al. |

FOREIGN PATENT DOCUMENTS

| | | |
|---|---|---|
| WO | WO-97/17919 A1 | 5/1997 |
| WO | WO-97/30700 A2 | 8/1997 |
| WO | WO-97/30700 A3 | 8/1997 |
| WO | WO-00/53139 A1 | 9/2000 |
| WO | WO-02/15816 A2 | 2/2002 |
| WO | WO-02/15816 A3 | 2/2002 |
| WO | WO-02/45698 A2 | 6/2002 |
| WO | WO-02/45698 A3 | 6/2002 |
| WO | WO-02/092783 A2 | 11/2002 |
| WO | WO-02/092783 A3 | 11/2002 |

OTHER PUBLICATIONS

3M Healthcare. (Date Unknown). "3M™ Steri-Strip™ S Surgical Skin Closure. Poster of Available Sizes," 3M HealthCare: St. Paul, MN, three pages.

3M Healthcare. (2001). "Reducing the Risk of Superficial Skin Damage Related to Adhesive Use," 3M HealthCare: St. Paul, MN, two pages.

3M Healthcare. (Jun. 27, 2002). "3M™ Steri-Strip™ Adhesive Skin Closures (reinforced): Commonly Asked Questions," 3M HealthCare: St. Paul, MN, pp. 1-4.

3M Healthcare. (2003). "Steri-Strip: Skin Closures," Product Insert, 3M HealthCare: St. Paul, MN, one page.

3M Healthcare. (May 2004). "Tips for Trouble-Free Taping," 3M HealthCare: St. Paul, MN, four pages.

3M Healthcare. (2006). "3M™ Steri-Strip™ S Surgical Skin Closure. The Simple, Non-Invase Alternative to Staples and Sutures from the Steri-Strip Family," HealthCare: St. Paul, MN, two pages.

3M Healthcare. (Oct. 19, 2006). "3M™ Steri-Strip™ S Surgical Skin Closure: Commonly Asked Questions," 3M HealthCare: St. Paul, MN, pp. 1-8.

3M Healthcare. (2007). "3M™ Steri-Strip™ S Surgical Skin Closure. Application Instructions," 3M HealthCare: St. Paul, MN, two pages.

3M Medical. (2006). "They Say Every Scar Tells a Story," 3M HealthCare: St. Paul, MN, one page.

3M Medical. (2006). "3M™ Steri-Strip™ S Surgical Skin Closure. Patient Care Information," 3M HealthCare: St. Paul, MN, two pages.

3M Medical. (2007). "3M™ Steri-Strip™ S Surgical Skin Closure. Application Examples, Comparisons and Results," 3M HealthCare: St. Paul, MN, four pages.

Aarabi, S. et al. (Oct. 2007). "Mechanical Load Initiates Hypertrophic Scar Formation Through Decreased Cellular Apoptosis," *The FASEB Journal* 21(12):3250-3261.

Al-Attar, A. et al. (Jan. 2006). "Keloid Pathogenesis and Treatment," *Plastic and Reconstructive Surgery* 117(1): 286-300.

Angelini, G.D. et al. (1984). "Comparative Study of Leg Wound Skin Closure in Coronary Artery Bypass Graft Operations," *Thorax* 39:942-945.

Anonymous (2003). "3M™ Steri-Strip™ Adhesive Skin Closures," 3M HealthCare Brochure, twelve pages.

Anonymous. (2005). "3M™ Tegaderm™ Family of Transparent Dressings," 3M HealthCare Brochure, six pages.

Anonymous. (2006). "Avocet Polymer Technologies," located at <http://www.avocetcorp.com/index.html>, last visited on Nov. 5, 2007, one page.

Anonymous. (2006). "Avogel Scar Hydrogel," located at <http://www.avocetcorp.com/avogel_scar_hydrogel.html>, last visited on Nov. 5, 2007, two pages.

Anonymous. (2006). "Avosil Ointment," located at <http://www.avocetcorp.com/avosil.html>, last visited on Nov. 5, 2007, three pages.

Anonymous. (Date Unknown). "Mepiform Instructions of Use," Tendra Corporation Brochure, two pages.

Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.

Atkinson, J-A.M. et al. (Nov. 2005). "A Randomized, Controlled Trial to Determine the Efficacy of Paper Tape in Preventing Hypertrophic Scar Formation in Surgical Incisions that Traverse Langer's Skin Tension Lines," *Plastic and Reconstructive Surgery* 116(6):1648-1656.

Bachert, B. et al. (2003). "Probing Elastic Modulus and Depth of a Two Layer Human Skin Model with Piezoelectric Cantilevers," Biomedical Enginerring Senior Design Team, Drexel University, 27 pages.

Berman, B. et al. (Mar. 3, 2005). "Keloid and Hypertrophic Scar," located at <http://www.emedicine.com/DERM/topic205.htm>, last visited on Jul. 7, 2006, 15 pages.

Bunker, T.D. (1983). "Problems with the Use of Op-Site Sutureless Skin Closures in Orthopaedic Procedures," *Annals of the Royal College of Surgeons of England* 65:260-262.

Burd, A. et al. (Dec. 2005). "Hypertrophic Response and Keloid Diathesis: Two Very Different Forms of Scar," *Plastic and Reconstructive Surgery* 116(7):150-157.

Canica Design Inc. (Date Unknown). "ABRA® Abdominal Wall Closure Set," located at <http://www.canica.com/instructions/1D1544RA%20-%20ABRA%20CWK08%20IFU.pdf>, last visited on Sep. 10, 2009, pp. 1-11.

Canica Design Inc. (Date Unknown). "ABRA® Surgical Skin Closure Set," located at <http://www.canica.com/instructions/1D0830RH.pdf>, last visited on Sep. 10, 2009, pp. 1-4.

Chen, H-H. et al. (Jul. 2001). "Prospective Study Comparing Wounds Closed With Tape With Sutured Wounds in Colorectal Surgery," *Arch. Surg.* 136:801-803.

Davison, S.P. et al. (Jan. 2006). "Ineffective Treatment of Keloids with Interferon Alpha-2b," *Plastic and Reconstructive Surgery* 117(1):247-252.

Escoffier, C. et al. (Sep. 1989). "Age-Related Mechanical Properties of Human Skin: An in Vivo Study," *J. Invest. Dermatol.* 9(3)3:353-357.

Evans, S.L. et al. (2009). "Measuring the Mechanical Properties of Human Skin in vivo Using Digital Correlation and Finite Element Modelling," *J. Strain Analysis* 44:337-345.

Fairclough, J.A. et al. (1987). "The Use of Sterile Adhesive Tape in the Closure of Arthroscopic Puncture Wounds: A Comparison with a Single Layer Nylon Closure," *Annals of the Royal College of Surgeons of England* 69:140-141.

Gorney, M. (Mar. 2006). "Scar: The Trigger to the Claim," *Plastic and Reconstructive Surgery* 117(3):1036-1037.

Hof, M. et al. (Jul. 2006). "Comparing Silicone Pressure-Sensitive Adhesives to Silicone Gels for Transdermal Drug Delivery," presented at 33 Annual Meeting and Exposition fo the Controlled Release Society, Vienna, Austria, Jul. 22-26, 2006, seven pages.

International Search Report and Written Opinion mailed on Feb. 7, 2008, for PCT Application No. PCT/US2007/017320, filed on Aug. 3, 2007, 11 pages.

Koval, K.J. et al. (Oct. 2003). "Tape Blisters Following Hip Surgery. A Prospective Randomized Study of Two Types of Tape," *The Journal of Bone and Joint Surgery* 855(10):1884-1887.

Kuo, F. et al. (May 2006). "Prospective, Randomized, Blinded Study of a New Wound Closure Film Versus Cutaneous Suture for Surgical Wound Closure," *Dermatological Surgery* 32(5):676-681.

Mustoe, T.A. et al. (Nov. 2005). "A Randomized, Controlled Trial to Determine the Efficacy of Paper Tape in Preventing Hypertrophic Scar Formation in Surgical Incisions that Traverse Langer's Skin Tension Lines," *Plastic and Reconstructive Surgery* (Discussion) 116(6):1657-1658.

Nahabedian, M.Y. (Dec. 2005). "Scar Wars: Optimizing Outcomes with Reduction Mammaplasty," *Plastic and Reconstructive Surgery* 116(7):2026-2029.

Northern Health and Social Services Board. (2005). *NHSSB Wound Management Manual*, pp. 1-97.

O'Brien, L. et al. (2009). "Silicon Gel Sheeting for Preventing and Treating Hypertrophic and Keloid Scars," *The Cochrane Collaboration* pp. 1-47.

Pitcher, D. (Feb. 1983). "Sutureless Skin Closure for Pacemaker Implantation: Comparison with Subcuticular Suture," *Postgraduate Medical Journal* 59:83-85.

Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.

Shirado, H. et al. (Mar. 2006). "Realization of Human Skin-Like Texture by Emulating Surface Shape Pattern and Elastic Structure," presented at Symposium on Haptic Interfaces for Virtual Environment and Teleoperator Systems 2006, Mar. 25-26, 2006, Alexandria, VA, pp. 295-196.

Smith & Nephew. (Date Unknown). "CICA-CARE. Silicone Gel Sheeting," located at <http://wound.smith-spehew.com/za/Product/asp?NodeId=569&Tab=5&hide=True>, last visited on Jun. 9, 2009.

Sullivan, S.R. et al. (2007). "Acute Wound Care," Chapter 7 in ACS Surgery: Principles and Practice, 24 pages.

Téot, L. (2005). "Scar Control" *European Tissue Repair Society*, located at <http://www.etrs.org/bulletin12_1/section11.php>, last visited on Nov. 6, 2007, 14 pages.

Vaughan, P. et al. (2006). "Optimal Closure of Surgical Wounds in Forefoot Surgery: Are Adhesive Strips Beneficial?" *Acta Orthop. Belg.* 72(6):731-733.

Vowden, K. (Mar. 2003). "Wound Management. Policy and Resource Pack," Bradford Teaching Hospitals NHS Foundation Trust, pp. 1-72.

Watson, G.M. (1983). "Op-Site Skin Closure: A Comparison with Subcuticular and Interrupted Sutures," *Annals of the Royal College of Surgeons of England* 65:83-84.

Webster, D.J.T. et al. (Sep. 1975). "Closure of Abdominal Wounds by Adhesive Strips: A Clinical Trial," *British Medical Journal* 20:696-698.

Westaby, S. (1980). "Evaluation of a New Product for Sutureless Skin Closure," *Annals of the Royal College of Surgeons of England* 62:129-132.

Wound Care Technologies. (2008). "DERMAClose™ RC: Continuous External Tissue Expander," located at < http://www.woundcaretech.com/sell-sheet.pdf>, last visited on Sep. 10, 2009, two pages.

Wound Care Technologies. (2008). "Instructions for Use. DERMAClose™ RC," located at < http://www.dermaclose.com/instructions.pdf>, last visited on Sep. 10, 2009, 2 pages.

\* cited by examiner

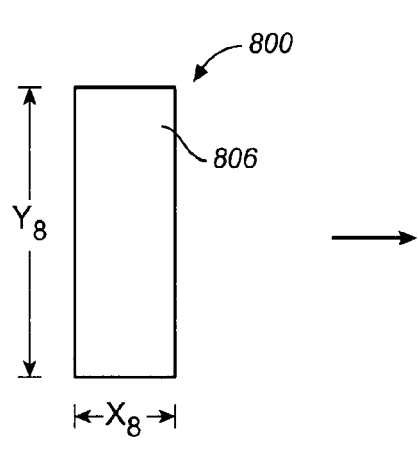
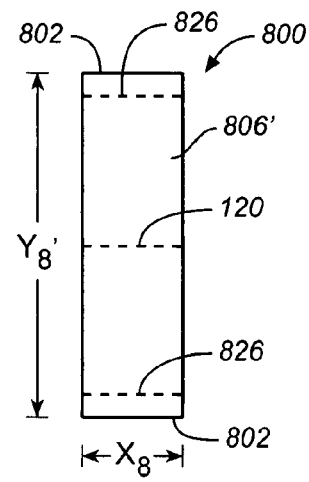
FIG. 8A     FIG. 8B
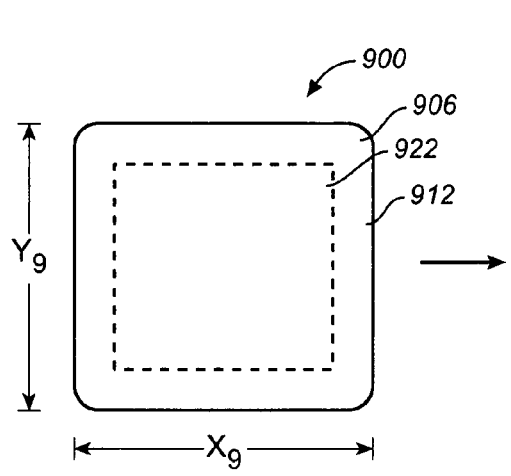
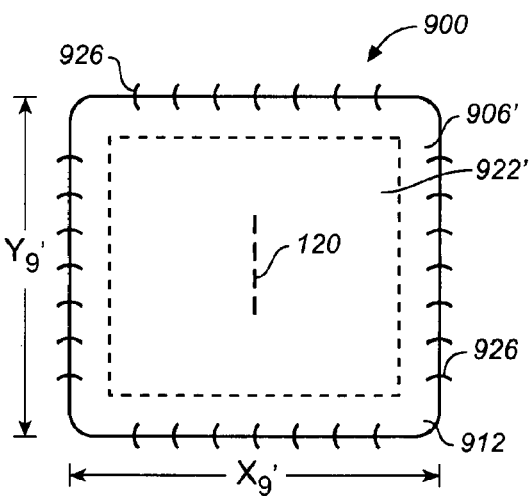
FIG. 9A     FIG. 9B

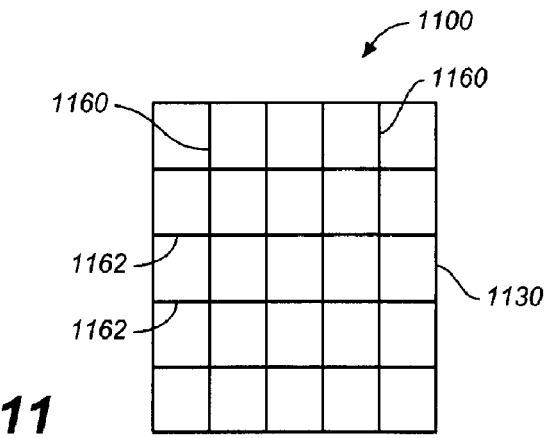
FIG. 11
FIG. 12A   FIG. 12B   FIG. 12C
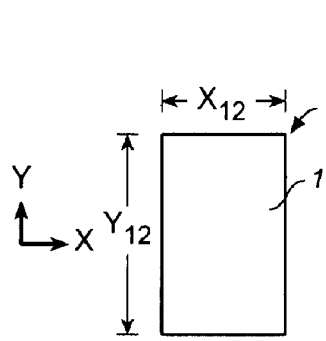 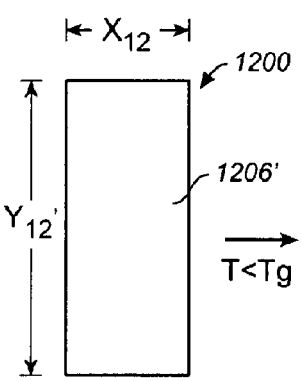 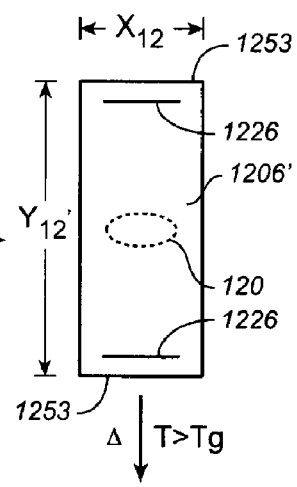
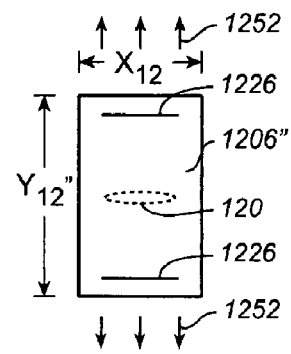
FIG. 12D

FIG. 14A
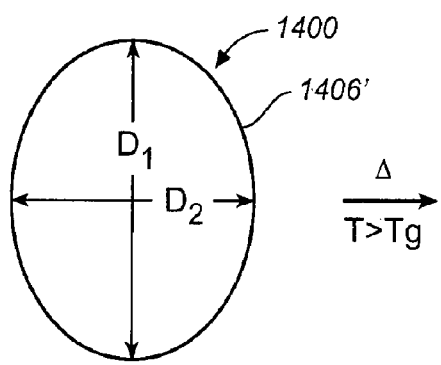
FIG. 14B
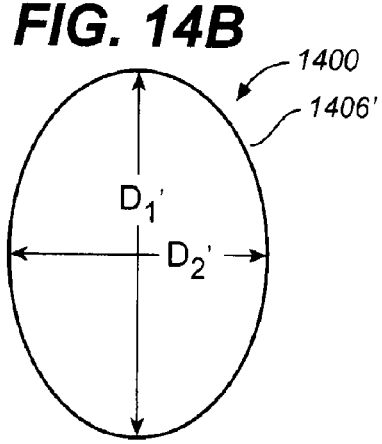
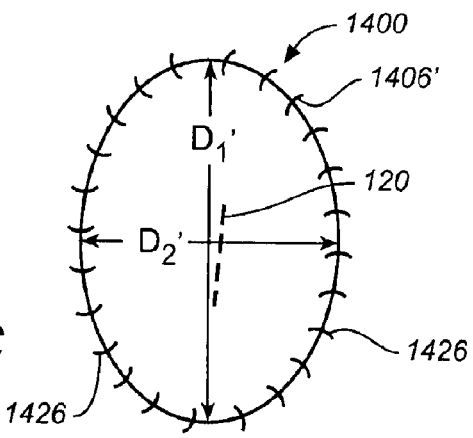
FIG. 14C
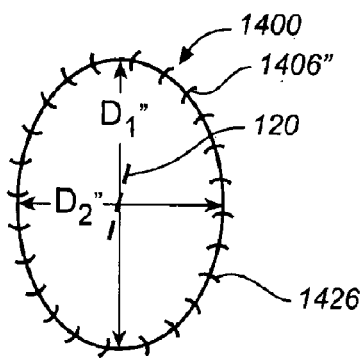
FIG. 14D

METHODS FOR THE TREATMENT OR PREVENTION OF SCARS AND/OR KELOIDS

CROSS REFERENCE TO RELATED APPLICATION

This application is a continuation of U.S. patent application Ser. No. 11/888,978, filed Aug. 3, 2007, which claims the priority benefit of U.S. Provisional Patent Application Ser. No. 60/835,654, filed Aug. 3, 2006, the disclosures of which are incorporated by reference herein in their entirety.

FIELD

The devices, kits and methods described herein are in the field of wound healing, and in particular, relate to scar treatment and the amelioration of scar formation. For example, the devices, kits and methods described herein may be used for the treatment, amelioration, or prevention of scars and/or keloids.

BACKGROUND

Scars form in response to cutaneous injury as part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and can occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress can increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

Devices and methods for preventing or ameliorating the formation of scars and/or keloids are therefore desirable.

SUMMARY

Described here are devices, bandages, kits and methods for ameliorating the formation of scars and/or keloids at a wound site. In general, the devices are removably secured to a skin surface in proximity to the wound site. The devices are configured to shield the wound from endogenous (i.e., dermal) or exogenous (i.e., physiological) stress, and in some variations, the devices are configured to shield the wound from both endogenous and exogenous stress.

The devices may comprise or be made from a polymer, such as a shape memory polymer (e.g., acrylate-based, styrene-based and epoxy-based shape memory polymers), or biocompatible silicone polymers. At least a portion of the devices may be made from a transparent material or at least a portion of the devices may be porous. The devices may or may not be occlusive, and in some variations, the devices are occlusive. Similarly, the devices may or may not comprise an aperture, and in some variations, the devices comprise at least one aperture.

The devices may be removably secured to the skin surface in a variety of ways. For example, the devices may be removably secured to the skin surface with an adhesive, with a skin piercing device, or the like. Suitable adhesives include pressure sensitive adhesives, such as polyacrylate-based, polyisobutylene-based, and silicone-based pressure sensitive adhesives. Suitable skin-piercing devices include microneedles, sutures, anchors, staples, microtines and the like.

The devices may have any suitable or desirable shape or size. For example, the devices may have a shape selected from the group consisting of rectangles, circles, squares, trapezoids, toroids, ovals, or segments and combinations thereof. For example, some devices may be substantially circular, others may be substantially toroidal, and still others may be substantially rectangular.

In some variations, the devices are configured to actively shield the wound from endogenous and/or exogenous stress. In other variations, the devices are configured to passively shield the wound from endogenous and/or exogenous stress. The devices may be configured to shield the wound from endogenous and/or exogenous stress in a dynamic fashion or static fashion.

The devices may also comprise an active agent. The active agent may be any suitable agent that may be useful in aiding in some aspect of the wound healing process. For example, the active agent may be a pharmaceutical compound, a protein (e.g., a growth factor), a vitamin (e.g., vitamin E), or combinations thereof. Of course, the devices may comprise more than one active agent, and the devices may deliver one or more active agents.

In some variations, it may be desirable for the device to comprise a mechanism for altering the temperature at the skin surface. The mechanism may be electrical, chemical, mechanical, or combinations thereof. In a similar fashion, the devices may include a mechanism to induce a color change in at least a portion of the device. For example, the color change can correspond to a change in device stiffness, device efficacy, or the like.

Bandages to ameliorate the formation of a scar and/or keloid at a wound site are also described. In general, the bandages are configured to be removably secured to a skin surface and have a first tensile-stressed configuration and a second relaxed configuration. In some variations, the first configuration is tensile stressed by about 5% relative to its relaxed configuration. In other variations, the first configuration is tensile stressed by about 10%, 15%, or 20% relative to its relaxed configuration. In still other variations, the first configuration is tensile stressed by about 25%, 30%, 35%, 40% 45%, 50%, 55%, 60%, 65%, 70%, 75%, 80%, 85%, 90%, 95% or 100% relative to its relaxed configuration. It should be understood that the term "about" qualifies each of these percentages.

The bandages may comprise a polymer, for example, a biocompatible silicone polymer, or a shape memory polymer. Suitable shape memory polymers were described above. As with the devices described above, the bandages may be removably secured to the skin surface in any desirable fashion, may include one or more active agents, may include a mechanism for altering the temperature at the skin surface, or may include a mechanism for inducing a color change in at least a portion of the bandage. Similarly, the bandages may have any suitable shape or size. At least a portion of the bandage may be made from a transparent material, and the bandages may or may not be occlusive.

Also described here are bandages for ameliorating the formation of a scar and/or keloid at a wound site, where the bandages comprise at least first, second, and third configurations. The second configuration is strained relative to the first configuration. The bandages are removably secured to a skin surface while in the second configuration and are capable of being activated while in the second configuration to adopt the third configuration. In some variations, the second configuration is thermally activated (e.g., by body temperature, a heating pad, an air blower, a heat gun, or the like) to adopt the third configuration.

In some variations, the second configuration is strained by about 5% relative to the first configuration. In other variations, the second configuration is strained by about 10%, about 15% or about 20% relative to the first configuration. In still other variations, the second configuration is strained by about 25%, 30%, 35%, 40%, 45%, 50%, 55%, 60%, 65%, 70%, 75%, 80%, 85%, 90%, 95%, or 100% relative to the first configuration. Again, the term "about" qualifies each of these percentages.

The third configuration may or may not be the same as the first configuration, and in some variations, the third configuration is substantially the same as the first configuration. In other variations, the third configuration differs from the second configuration in at least one direction. In still other variations, the third configuration differs from the second configuration in at least two directions. In some variations, the third configuration differs from the first configuration by less than about 10% in at least one direction. In other variations, the third configuration differs from the first configuration by less than about 10% in at least two directions. In some variations, the third configuration is at least partially determined by the constraint placed on the bandage, which may or may not be affected by skin compliance.

Also described here are kits for ameliorating the formation of scars or keloids. The kits comprise in packaged combination at least two devices. Each device is configured to be removably secured to a skin surface in proximity to a wound site and to shield the wound from endogenous and/or exogenous stress. In some variations of the kits, the devices have different colors or shapes. The devices may also have different sizes or thicknesses. The at least two devices may be configured to shield the wound from endogenous and/or exogenous stress by different amounts. The kits may also comprise instructions on how to use the devices, an air blower, a heat gun, a heating pad, a wound dressing, at least one wound cleanser, and other suitable or useful materials.

Methods for ameliorating the formation of scars or keloids are also described. In general, the methods comprise applying to skin, in the proximity of a wound, a device configured to shield the wound from endogenous and/or exogenous stress. The device may be applied at any appropriate time during the wound healing process, and in some variations, the device is applied during the proliferative phase of wound healing. Similarly, the device may be applied to the wound for any suitable length of time. For example, the device may be applied to the wound for at least about 10 days, at least about 20 days, at least about 30 days, at least about 40 days, at least about 50 days, at least about 60 days, at least about 70 days, at least about 80 days, at least about 90 days, or at least about 100 days. In some variations, the device may be applied to the wound for longer periods, e.g., for about 6 months, about 9 months, about 12 months, or about 15 months. In some variations, the methods comprise removing the device after a period of time, which may or may not be predetermined.

The methods may also comprise applying to the skin, in the proximity of the wound, a second device. The second device may be configured to shield the wound from endogenous and/or exogenous stress or may be configured to be removably secured to a skin surface and configured to reduce stress on the wound in at least one direction.

BRIEF DESCRIPTION OF THE DRAWINGS

FIGS. 8A-B are top views of a device or bandage having a first tensile stressed configuration that is stressed primarily in one direction.

FIGS. 9A-B are top views of a device or bandage having a first tensile stressed configuration that is stressed in two directions.

FIG. 11 illustrates a device comprising wires or fibers.

FIGS. 12A-D illustrate a device or bandage having a first configuration, a strained second configuration attached to skin, and a third configuration attached to skin. The third configuration differs from the second configuration in one direction.

FIGS. 14A-D illustrate another variation of a device or bandage having a third configuration differing from a second configuration in two directions.

DETAILED DESCRIPTION

Figure 1:
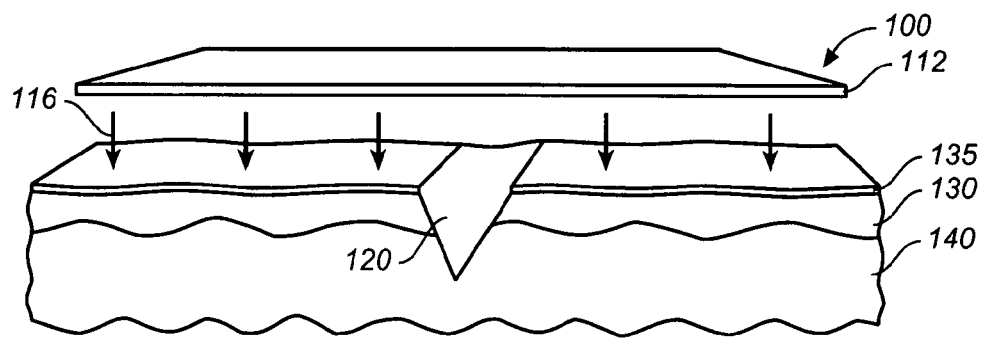
FIG. 1 is a schematic view of an illustrative device applied to a skin surface in the proximity of a wound site.

The mechanical environment of an injury can be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The skin includes the outer stratum corneum, the epidermis and dermis. The devices, bandages, kits and methods described herein can control or regulate the mechanical environment of a wound to ameliorate scar and/or keloid formation. The mechanical environment of a wound includes stress, strain, and any combination of stress and strain. The control of a wound's mechanical environment can be active or passive, dynamic (e.g., by applying an oscillating stress) or static. Devices and methods described here can shield a wound from its mechanical environment. The term "shield" is meant to encompass the unloading of stress experienced by the wound as well as providing a physical barrier against contact, contaminants, and the like. The devices and methods described here can shield a wound by unloading the wound and surrounding tissues from endogenous stress and/or exogenous stress. Thus, devices and methods described here can reduce the stress experienced by a wound and surrounding tissues to a lower level than that experienced by normal skin and tissue. Unloading of exogenous and/or endogenous stress in the vicinity of the wound can ameliorate the formation of scars, hypertrophic scars, or keloids.

A cell's external mechanical environment can trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

Wound Healing and Scar and Keloid Formation

As noted above, the wound healing process occurs in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase can continue for many weeks or months, or indefinitely after injury. Scars typically reach about 75-80% of normal skin breaking strength 6-8 weeks after injury. In general, scars typically have a triangular cross-section. That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that inducing mechanical strain early in the proliferative phase of the wound healing process inhibits cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids.

Devices

Devices are described here for ameliorating the formation of scars and/or keloids at a wound site. The scars may be any type of scar, e.g., a normal scar, a hypertrophic scar, etc. In general, the devices are configured to be removably secured to a skin surface near a wound. The devices can shield the wound from endogenous stress originating from the skin itself (e.g., stress transferred to the wound via the stratum corneum, epidermal or dermal tissue), and/or exogenous stress (e.g., stress transferred to the wound via physical body movement or muscle action). In some variations, the devices shield the wound from endogenous stress without affecting exogenous stress on the wound, e.g., devices that modify the elastic properties of the skin, etc. In other variations, the devices shield the wound from exogenous stress without affecting endogenous stress on the wound. Such variations can include situations where the musculature and surrounding wound tissue has been paralyzed, e.g., through the use of botulinim toxin or the like. In still other variations, the devices shield the wound from both endogenous and exogenous stress.

The devices and bandages described here may ameliorate the formation of scars at wound sites by controllably stressing or straining the epidermis and deeper layers of dermal tissue around the wound, thereby reducing tensile or compressive stress at the wound site itself. The stress at the wound site can be reduced to levels below that experienced by normal skin and tissue. The stress or strain can be applied to surrounding tissue in one, two, or three directions to reduce endogenous or exogenous stress at the wound in one, two or three directions.

Referring to FIG. 1, device or bandage 100 comprises a body 112, that is removably secured to skin surface 135 near wound site 120, as indicated by arrows 116. The device 100 can be removably secured to the skin surface (e.g., stratum corneum and epidermis) 135 by an adhesive, or by using one or more skin piercing devices (e.g., sutures, anchors, microneedles, staples, etc.), or the like. In some variations, the devices are removably secured to the tissue below the skin surface, e.g., sutures, anchors, staples, and the like can be used to removably secure the devices to the deepest layers of the dermis down to the fascia. In the variation illustrated in FIG. 1, wound 120 extends beneath the epidermis 135 through dermis 130 to reach the hypodermis or subcutis 140. Although device 100 is depicted as a single layer in FIG. 1 for simplicity, the devices described here can comprise multiple layers and have any number of different configurations. In some variations, the devices comprise multiple layers that remain separate. In other variations, the devices comprise multiple layers in an overlay configuration. In still other variations, the devices comprise multiple layers that are joined or welded together, e.g., in a laminate.

Figure 2A:
FIG. 2A is a cross-sectional view of an illustrative device having an adhesive layer.
Figure 2B:
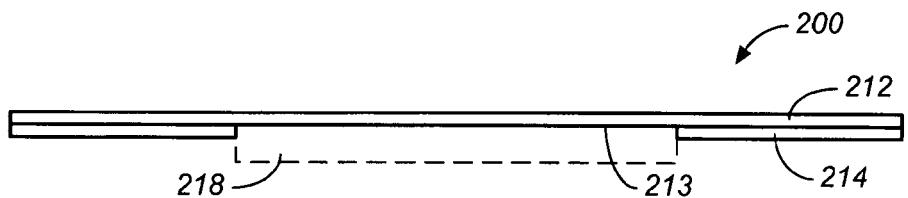
FIG. 2B is cross-sectional view of a device having an adhesive layer and a wound dressing.
Figure 2C:
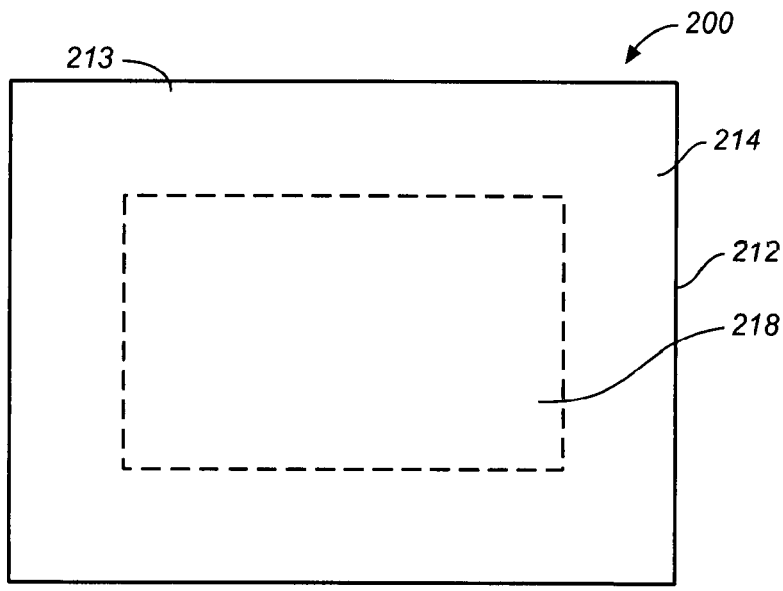
FIG. 2C is a bottom view of the device shown in FIG. 2B.
Figure 3A:
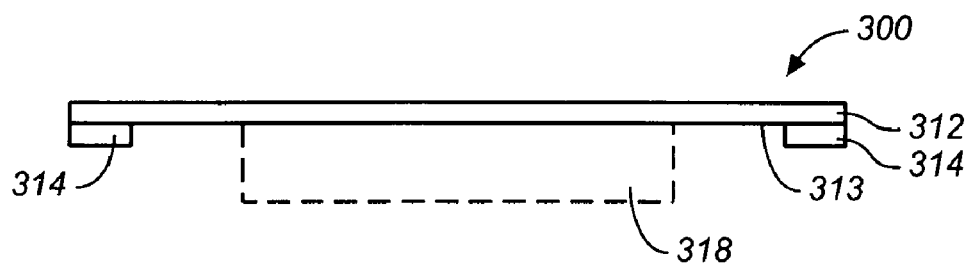
FIG. 3A is cross-sectional view of an illustrative device having an adhesive layer and a wound dressing.
Figure 3B:
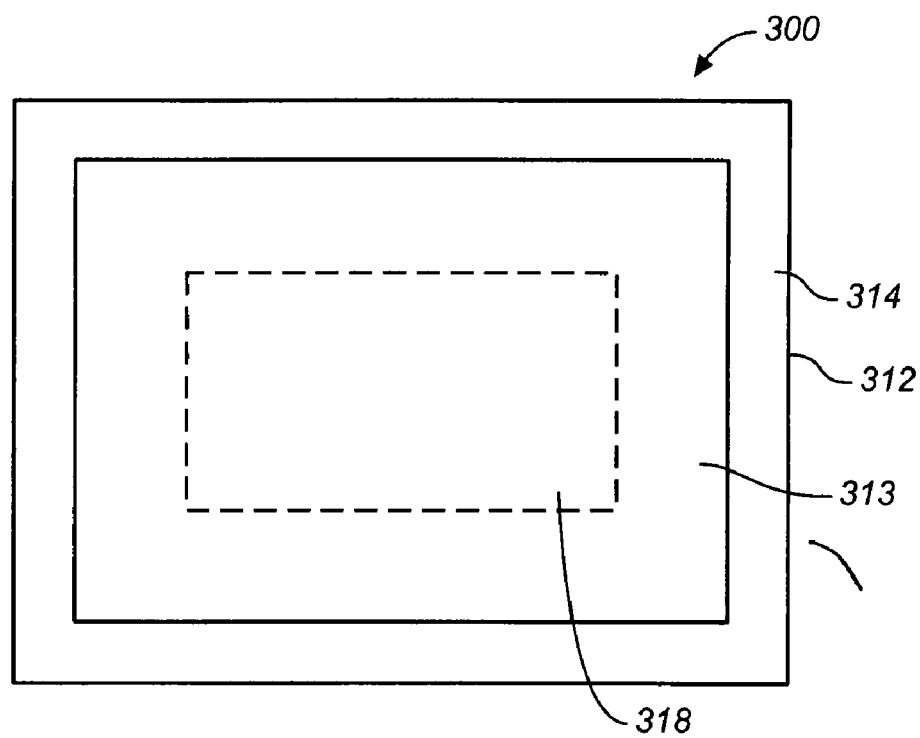
FIG. 3B is a top view of the device shown in FIG. 3A.

As shown in FIG. 2A, the device 200 may include an adhesive layer 214 for removably attaching device 200 to the skin. The adhesive layer can be applied in any suitable fashion to surface 213 of body 212 that is intended to contact the skin. For example, adhesive layer 214 can be a continuous layer around the periphery of surface 213. In other variations, adhesive layer 214 can be a continuous layer substantially covering surface 213. Adhesive layer 214 may be a contiguous or noncontiguous layer on surface 213. In some variations, adhesive layer 214 comprises a pressure sensitive adhesive, e.g., polyacrylate-based, polyisobutylene-based, silicone-based pressure sensitive adhesives, and the like. As shown in FIG. 2B, in some variations, device 200 can include an optional wound dressing 218 to be applied to a wound (not shown). The surface 213 of device 200 that is intended to contact the skin is shown in FIG. 2C. In this variation, adhesive layer 214 and wound dressing 218 in combination substantially cover surface 213. In some variations (not shown), a wound dressing can be placed over at least a portion of an adhesive layer. Alternatively, as shown in FIGS. 3A-B, adhesive layer 314 of device 300 can partially cover surface 313 of body 312, for example by forming a frame around the periphery of surface 313. Optional wound dressing 318 can be located centrally within the frame formed by adhesive 314.

Figure 4A:
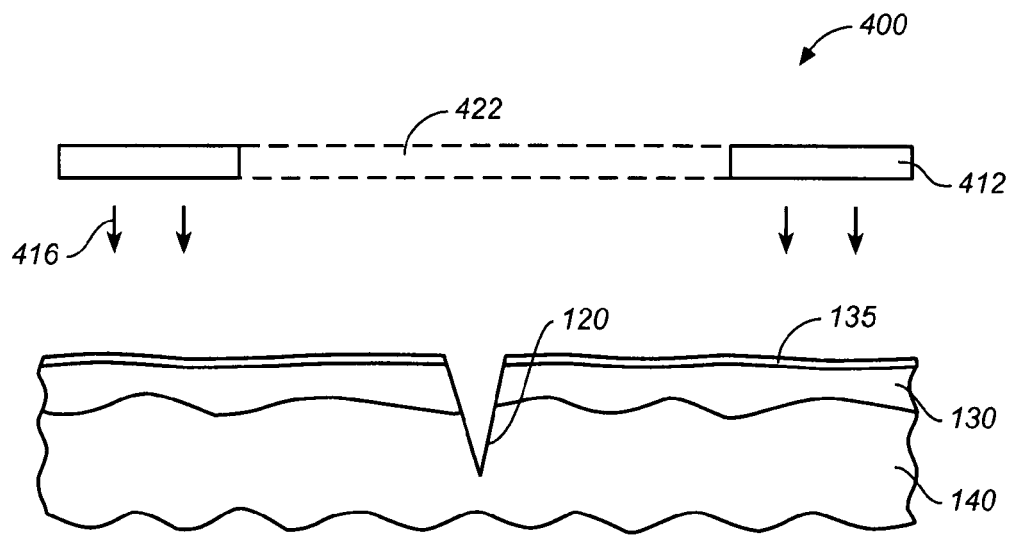
FIG. 4A is a cross-sectional view of a device having an aperture.
Figure 4B:
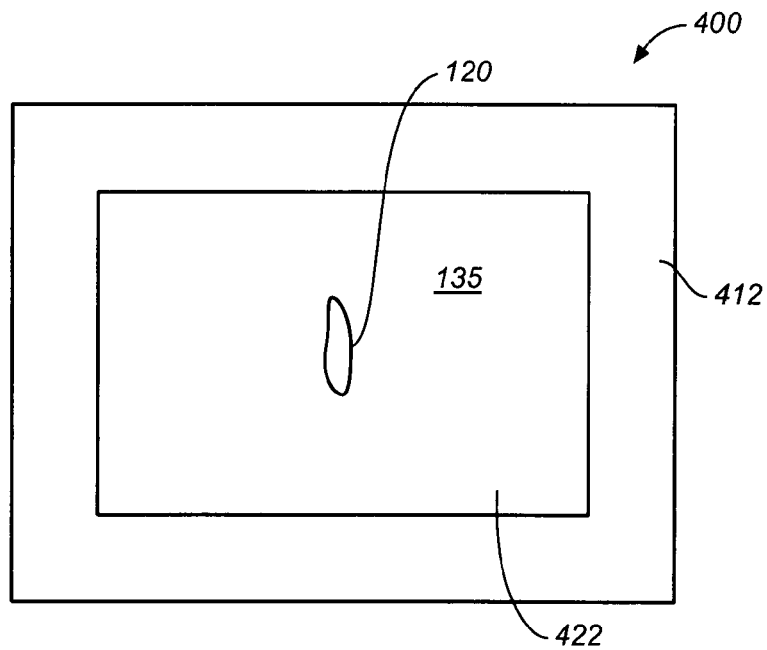
FIG. 4B is a top view of the device shown in FIG. 4A.
Figure 5:
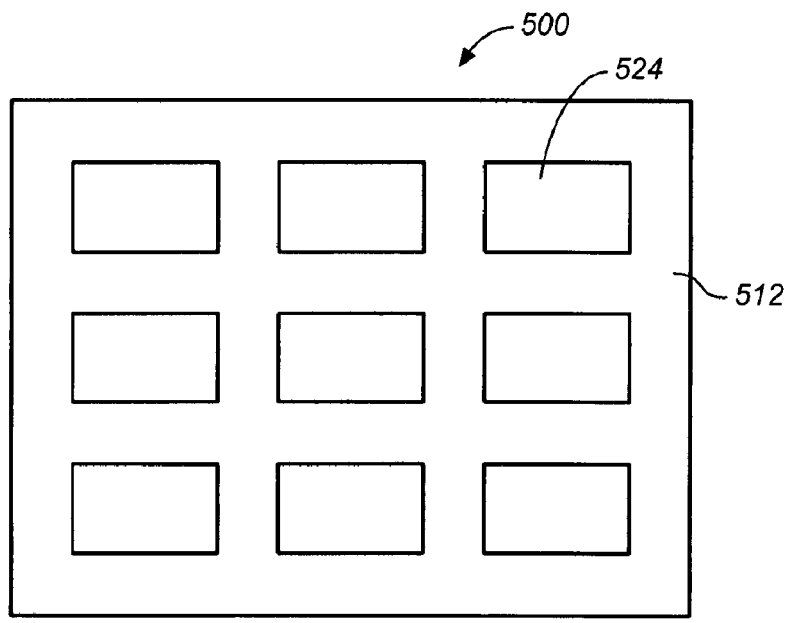
FIG. 5 is a top view of a device having multiple apertures.

The body of the device need not be solid. For example, as shown in side and top views respectively in FIGS. 4A-B, device 400 can comprise a body 412 that includes at least one aperture 422. Aperture 422 can be positioned to surround wound 120 as shown by arrows 416. As shown in FIG. 5, device 500 can comprise a body 512 that includes multiple apertures 524. Although FIG. 5 depicts apertures 524 arranged in a lattice fashion, the apertures can be arranged randomly or in any suitable fashion, e.g., in rows, columns, in a circle, an oval, or on a diagonal. The apertures (e.g., apertures 422, 524 in FIGS. 4 and 5) may also be of any suitable shape, e.g., square, rectangle, quadrilateral, oval, round, etc. The apertures may also have any suitable size. In addition, the apertures may be cut into the devices in a contour according to the shape of the wound. For example, for an elongate wound, an aperture such as aperture 422 in FIG. 4 can have an elongate shape, with the long axis of the aperture approximately parallel to the long axis of the wound. In other variations involving an elongate wound, an aperture such as aperture 422 in FIG. 4 can have an elongate shape, with the long axis of the aperture approximately orthogonal to the long axis of the wound. In these variations, the apertures may be cut by the user or attending physician, immediately prior to use.

Figure 6:
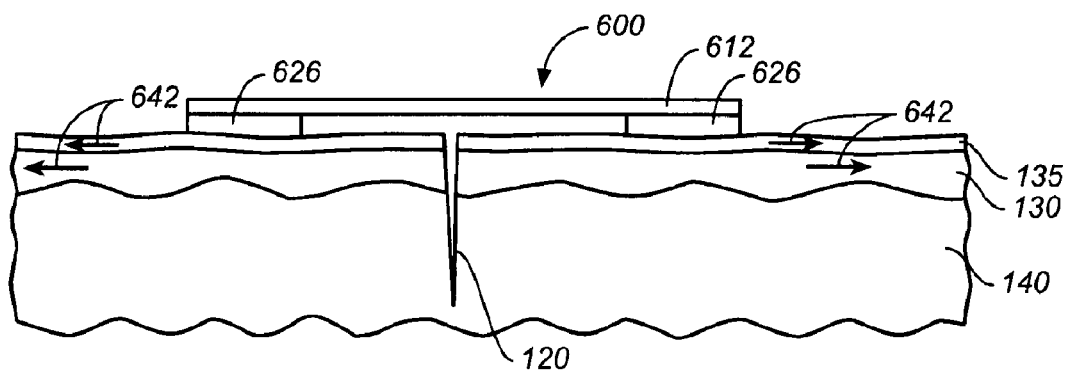
FIG. 6 is a cross-sectional view of a device or bandage secured to a skin surface in the proximity of a wound site.

As noted above, the devices and bandages described here shield the wound from endogenous and/or exogenous stress. Referring to FIG. 6, device 600 is removably secured to the stratum corneum (not shown) and epidermis 135 by a securing mechanism 626. As described above, securing mechanism 626 may be anything suitable for removably securing the device 600 to the skin surface near a wound site, e.g., an adhesive, a staple, a suture, a microneedle, an anchor, or the like. If an adhesive is used as the securing mechanism, the adhesive can be selected to exhibit minimal creep over time. For example, the rheological properties of adhesives can be tuned. One method of tuning rheological properties of adhesives includes the addition of cross linking agents to increase the cross link density of the adhesive, e.g., a pressure sensitive adhesive. Suitable cross linking agents can include highly functionalized molecules such as aluminum acetylacetonate. The cross linking density of an adhesive can be adjusted to achieve desirable adhesion values while minimizing the amount of creep the adhesive will demonstrate over time. When the devices are sutured, anchored or stapled to the skin, the devices may be attached to the dermis 130 or subcutis 140 as well as epidermis 135. This may help improve isolation or unloading of the wound from exogenous and/or endogenous stress.

The devices may be applied to a wound site at any suitable time. For example, in some variations, it is desirable to apply the devices to the wound site from about one to about three days following injury, i.e., during an initial period such as the early part of the proliferative phase. It should be understood that the devices may or may not be applied to a wound site where the wound has already initially been closed (e.g., by suturing, adhesives, bandages or the like). Similarly, the devices may be applied to a fresh wound caused by a scar removal procedure. In some instances, the device will be applied up to seven days following injury, i.e., later in the proliferative phase. For example, swelling and wound exudates may indicate that the devices be applied later than three days following injury. In some applications, a first bandage can be applied within an initial period following injury, e.g., within the first three days, and then removed, and a second bandage can be applied thereafter. The second bandage can be adapted to changes in the skin and tissue surrounding the wound that can occur after the initial period, e.g., decreased swelling and exudates.

Referring again to FIG. 6, after device 600 is attached to the skin proximate a wound site, device 600 is contracted as body 612 is contracted in at least one direction. As device 600 is contracted, tension is transferred to the skin at or external to securing mechanisms 626 as indicated by arrows 642, thereby reducing stress at the wound site. By adjusting the amount and direction of contraction in device 600, wound 120 can be effectively isolated from exogenous and/or endogenous stress in many instances. That is, device 600 can operate to unload wound 120 and surrounding tissue from endogenous forces from skin tension as well as exogenous forces from muscle action and body movement. In this manner, scar formation at wound 120 may be reduced.

The devices and bandages described herein may have any suitable shape. For example, the devices or bandages may be rectangular, square, circular, oval, toroidal, or segments or combinations thereof. In many variations, the devices will be flexible and planar to allow conformal placement against skin. Of course, the devices and bandages may also be of any suitable size, to deal with a variety of wounds. In some variations, the devices and bandages may be cut immediately prior to use from a roll or sheet of bandage to ensure appropriate coverage of the wound site. Devices and bandages can extend out to about 20 cm (about 8 inches) from the wound in some instances, and in other instances the devices or bandages can extend about 2, 4, 6, 8, 10, 12, 14, 16, or 18 cm from the wound, where "about" qualifies each of the distances. In still other variations, the bandages can extend about 22 cm, about 24 cm, about 26 cm, or even more, from the wound. In some variations, the devices are made from a polymer, for example, a shape memory polymer. Any suitable shape memory polymer may be used, e.g., styrene-based, epoxy-based, or acrylate-based shape memory polymers.

The devices and bandages may or may not be occlusive, and in some variations, the devices and bandages are occlusive. At least a portion of the devices and bandages may also be made of a transparent material. The transparent material can be placed over the wound to allow monitoring of the wound (e.g., to monitor infection or healing progress). In some variations, the devices or bandages described herein can be perforated, partially perforated, or at least partially porous. For example, some variations of the devices and bandages allow oxygen and/or moisture exchange with the environment.

The devices and bandages may also include a mechanism for increasing the temperature at the skin surface where the device or bandage is applied. This may be beneficial, for example, to aid in the healing process. The mechanism may be electrical, e.g., a resistive heating element, chemical, e.g., an exothermic chemical reaction, or mechanical, e.g., the creation of an element that friction rubs, e.g., against the skin.

The bandages and devices described here may also comprise a mechanism to induce a color change in at least a portion of the bandage. This may be helpful, for example, to alert the user to the device's decreasing efficacy, stiffness or the like. In some variations, a color change in a device or bandage may correspond to a change in bandage stiffness. For example, if a device or bandage is strained or stressed, at least a portion of the device or bandage may have a different color than when it is relaxed. Similarly, a color change in a device or bandage may correspond to a change in bandage efficacy. For example, at least a portion of the device or bandage may change color as its moisture content changes. In other variations, a device or bandage may change color after a predetermined period of time.

The devices and bandages described here may also comprise or deliver one or more active agents. Active agents can assist in wound healing, and may therefore include any suitable compound. For example, the active agent may be a pharmaceutical compound, a protein, a vitamin, or the like. Illustrative active agents that may be desirable for use with the bandages and devices described here include, but are not limited to growth factors, enzymes such as elastase to degrade the extra cellular matrix, proteases such as aspartate, serine, and metalloproteases that are capable of digesting and remodeling tissue, inhibitors of enzymes such as tissue inhibitors of metalloproteases, antibiotics, antifungals, vitamin E, and combinations thereof. In some variations, delivery of active agents can be controlled by time-release, e.g., by encapsulating or embedding the active agents in a time-release formulation, such as a drug delivery polymer or depot.

Figure 7A:
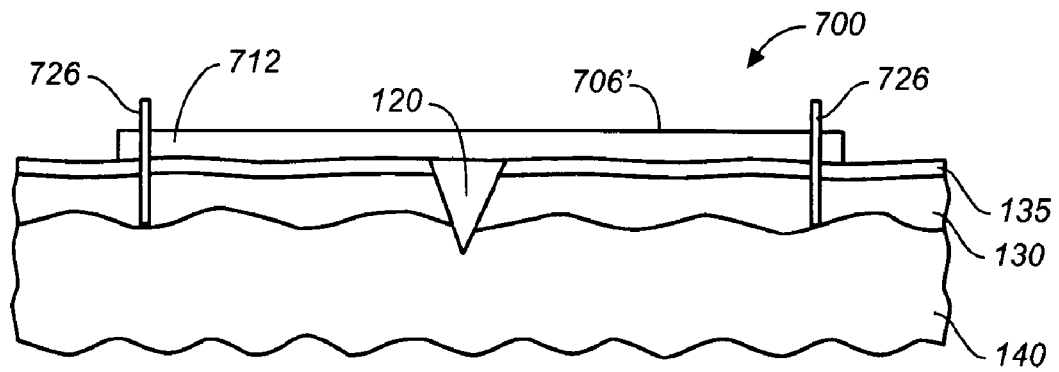
FIG. 7A is a cross-sectional view of a device or bandage having a first tensile stressed configuration that is secured to a skin surface in the proximity of a wound site.
Figure 7B:
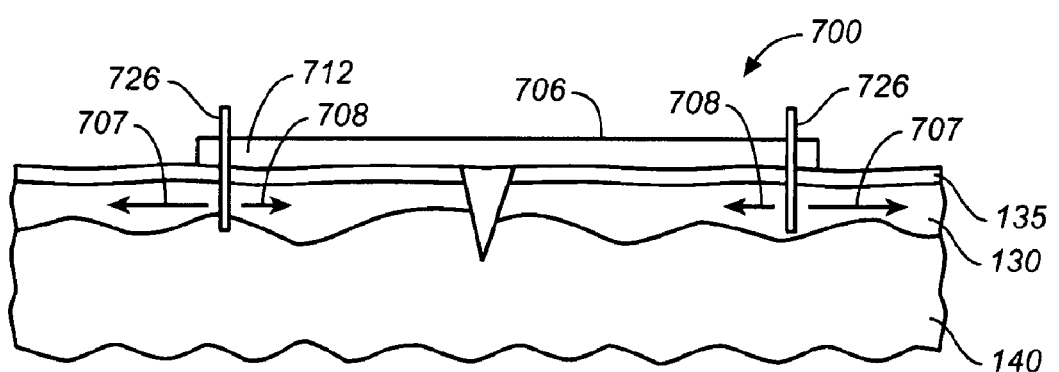
FIG. 7B is a cross-sectional view of the device shown in FIG. 7A in a relaxed configuration.

In some variations, the bandages for ameliorating the formation of a scar and/or keloid at a wound site have a first tensile stressed configuration (e.g., as shown in FIG. 7A) and a second relaxed configuration (e.g., as shown in FIG. 7B). For example, as illustrated in FIG. 7A, device or bandage 700 having body 712 can be removably secured to the skin surface or epidermis 135 near wound 120 via securing mechanisms 726 while in first configuration 706'. As shown in FIG. 7A, configuration 706' is tensile stressed in at least one direction. In some variations, device 700 is removably secured to dermis 130 as well as epidermis 135 via securing mechanisms 726, e.g., using sutures, anchors, staples, microneedles or the like. In still other variations, device 700 is removably secured to the tissue deeper than dermis 130. As discussed above, if an adhesive is used as a securing mechanism, the adhesive can be selected to exhibit minimized creep properties over time, e.g., by adjusting the cross link density in the adhesive. The cross linking density of an adhesive can be adjusted to achieve desirable adhesion values while minimizing the amount of creep demonstrated by the adhesive. When tensile stress is removed from device 700, it will adopt a relaxed configuration 706 shown in FIG. 7B, stressing tissue at or external to securing mechanisms 726, as indicated by arrows 707. In this way, the wound tissue underneath the device 700 is pulled inward to reduce stress at the wound, as indicated by arrows 708. The first tensile stressed configuration 706' may be stressed relative to relaxed configuration 706 by about 5%, 10%, 15%, 20%, 25%, 30%, 35%, 40%, 45%, 50%, 55%, 60%, 65%, 70%, 75%, 80%, 85%, 90%, 95%, or 100%. It should be understood that the term "about" qualifies each of these percentages. By adjusting the amount and directionality of stress in tensile stressed configuration 706', stress at the wound site 120 may be minimized. That is, the device can shield the wound and tissue from endogenous and/or exogenous stress. In some instances, the device can reduce stress at the wound site such that it is lower than stress experienced by typical, unscarred skin. Further, the stress in tensile stressed configuration 706' may be adjusted for different skin types and thicknesses to shield, i.e., unload, wounds from endogenous stress. In addition, the stress in tensile stressed configuration 706' may be adjusted to accommodate different ranges of motion to shield, e.g., unload, wounds from exogenous stress.

In the variation illustrated in FIGS. 8A-B, a bandage 800 in its relaxed configuration 806 has an X-direction (width) $X_8$ and a Y-direction (length) $Y_8$. As shown in FIG. 8B, bandage 800 can be tensile stressed, i.e., stretched, in at least one direction to form tensile stressed configuration 806'. In this variation, bandage 800 is tensile stressed in the Y-direction to length $Y_8'$, but remains substantially unstressed in the X-direction to approximately retain width $X_8$. Bandage 800 in its stressed configuration 806' can then be placed over wound 120 and removably secured to the skin surface via securing mechanisms 826. In this variation, securing mechanisms 826 are located proximate to bandage edges 802. The tensile stress on bandage 800 may isolate and shield wound 120 from endogenous and/or exogenous stress in the Y-direction.

In the variation illustrated in FIGS. 9A-B, a bandage 900 in its relaxed configuration 906 has width $X_9$ and length $Y_9$. As shown in FIG. 9B, bandage 900 with body 912 and optional aperture 922 can be tensile stressed in at least two directions to form tensile stressed configuration 906' having width $X_9'$ and length $Y_9'$. Stressed configuration 906' can then be applied over wound 120, e.g., to frame wound 120 in stressed aperture 922', and removably secured to the skin surface via securing mechanisms 926. Bandages such as bandage 900 that are tensile stressed in at least two directions may shield, i.e., unload, wounds from endogenous and/or exogenous stress in at least two directions.

In some variations, the first tensile stressed configuration can be mechanically induced. For example, devices or bandages can include at least one spring element. The spring element can be extended to form a tensile stressed configuration, and the spring element can be released to form a relaxed configuration. Alternatively, the devices or bandages may comprise an elastic material, such as a biocompatible polymer, e.g., silicone The elastic material may be stretched to form a tensile stressed configuration. In other variations, the first tensile stressed configuration may be at least partially induced by at least one piezoelectric element. In still other variations, the first tensile stressed configuration may be induced electrostatically. In some variations, the bandage is made of a shape memory polymer, and is therefore easily made to have a first tensile stressed configuration and a second relaxed configuration. The devices or bandages may be tensile-stressed in a dynamic fashion, e.g., by applying an oscillating force to the bandages or devices. For example, if a bandage includes a piezoelectric element, an alternating potential can be applied to the piezoelectric element, causing the device to alternately expand and contract in at least one direction. Similarly, if a bandage includes an electrostatic element, an alternating potential can be applied to the electrostatic element to cause it to alternately expand and contract in at least one direction.

Some bandages comprise at least first, second and third configurations. In these variations, the second configuration is typically strained relative to the first configuration. The bandages are configured to be removably secured to a skin surface while they are in the second configuration and are capable of being activated while in the second configuration to adopt a third configuration. In some variations, the second configuration can be thermally activated to adopt the third configuration. For example, body heat, a heating pad, an air blower, a heat gun, or the like may be used activate the second configuration to adopt the third configuration.

The first configuration may be "stored" in the bandages. For example, the when a biocompatible, non-shape memory polymer is used, e.g., such as a silicone polymer sheet, the first configuration may be stored by stretching the polymer sheet and then clamping the sheet along its edges to a stiffer polymer sheet using any suitable attachment device. The bandage may or may not be allowed to relax for a period of time (e.g., about 5 minutes, about 10 minutes, about 20 minutes, etc.) before application to skin. If a bandage comprises a shape memory polymer, the first configuration may be stored by crosslinking a polymeric sheet to form a flexible first configuration. Above the glass transition temperature $T_g$ of the polymer, the polymer can be deformed or strained to adopt a second configuration. The second strained configuration can be stabilized or "locked in" by cooling the polymer to a temperature substantially below $T_g$ of the polymer while maintaining the strain. In many variations, the strained configuration can be stabilized by cooling the shape memory polymer at least about 10, about 20, about 30 or about 50° C. below $T_g$. In some instances, the shape memory polymer may be cooled more than about 50° C. below $T_g$. The strained second configuration can be stabilized indefinitely if stored at a temperature sufficiently below $T_g$. For example, in many variations, the strained state of a shape memory polymer bandage can be stored indefinitely at a temperature more than about 20° C. lower than $T_g$. In some variations, the polymer bandage can be stored in its strained configuration at a temperature about 15° C. or about 10° C. below $T_g$. If the polymer is heated above $T_g$ and is not significantly loaded or constrained, then the polymer may approximately recover to its original first configuration. Thus, in some variations, the third configuration may be approximately the same as the first configuration. If the polymer is loaded or constrained, it may adopt a third configuration that is intermediate between the first and second configurations. That is, a shape memory polymer bandage in the second configuration heated above $T_g$ may at least partially recover its first configuration, subject to constraint experienced by the bandage. For example, the recovery of a strained configuration of a shape memory polymer bandage attached to skin may be affected by the compliance of the skin. Shape memory polymers can be selected to have $T_g$ compatible with use on human skin, e.g., from about 35° C. to about 55° C. In some variations, a device may include one or more thermally insulating layers that allow the use of shape memory polymer having $T_g$ higher than about 55° C. Higher $T_g$ materials may have increased elastic stiffness and reduced creep deformation over time.

In some variations, the third configuration of the bandages can differ from the strained second configuration in at least one dimension or direction. In other variations, the third configuration can differ from the strained second configuration in at least two directions. In some variations, the third configuration differs from the initial first configuration by less than about 10%, about 20%, about 30%, about 40%, about 50% or about 60% in at least one direction. In other variations, the third configuration differs from the initial configuration by less than about 10%, about 20%, about 30%, about 40%, about 50% or about 60% in at least two directions. In some variations, the second configuration is strained by about 5%, 10%, 15%, 20%, 25%, 30%, 35%, 40%, 45%, 50%, 55%, 60%, 65%, 70%, 75%, 80%, 85%, 90%, 95%, or 100% relative to the first configuration. It should be understood that the term "about" qualifies each of these percentages. By adjusting the amount and directionality of strain in the strained configuration, stress at a wound site may be minimized. That is, the amount and directionality of strain in prestrained devices or bandages can be adjusted for different skin types, thicknesses and conditions to shield, i.e., unload, wounds from endogenous stress. In addition, the amount and directionality of strain in prestrained devices or bandages can be adjusted to accommodate different ranges of motion or muscle action to shield wounds from exogenous stress.

Figure 10A:
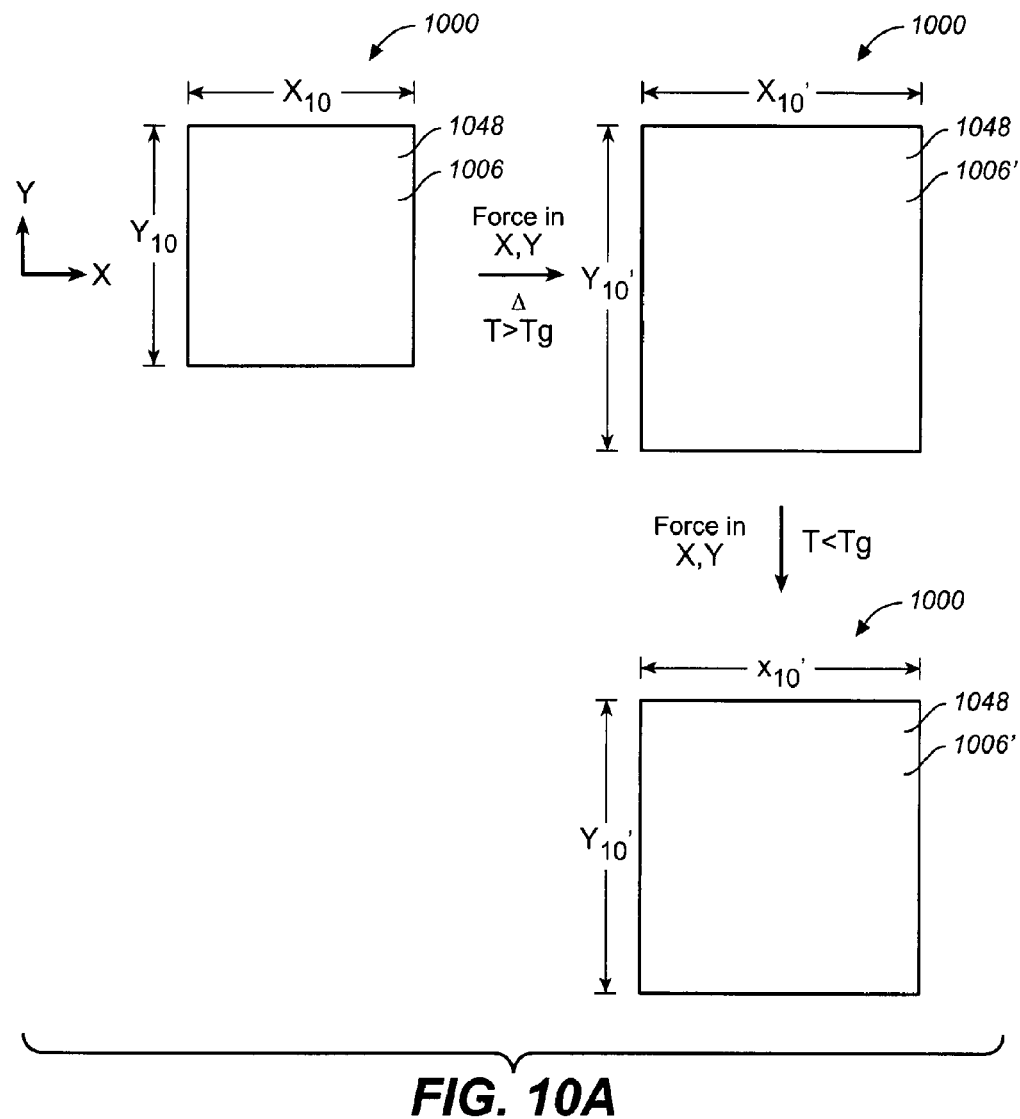
FIG. 10A provides top views of a variation of a device or bandage having a first configuration and a second configuration, where the second configuration is strained relative to the first configuration.
Figure 10B:
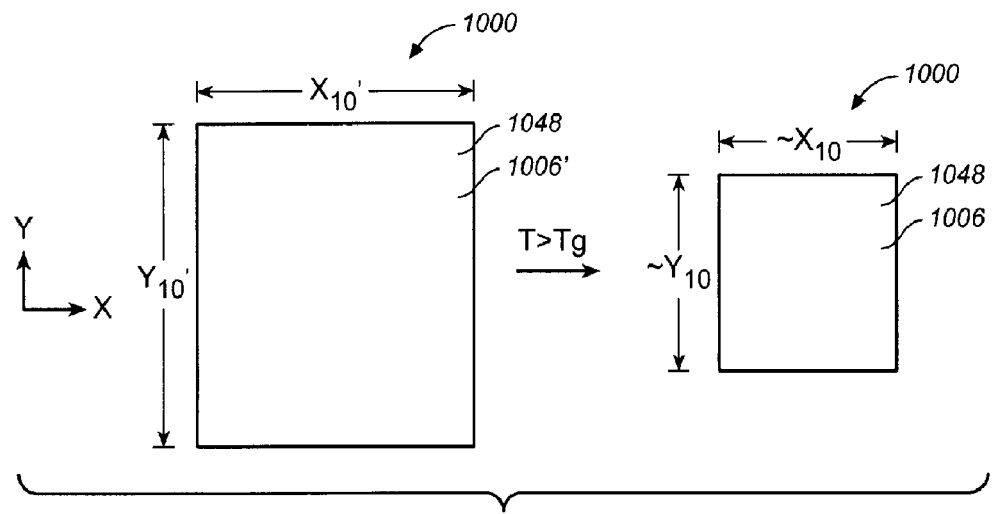
FIG. 10B shows the recovery of the strained configuration of the device or bandage illustrated in FIG. 10A in the absence of significant constraint.
Figure 10C:
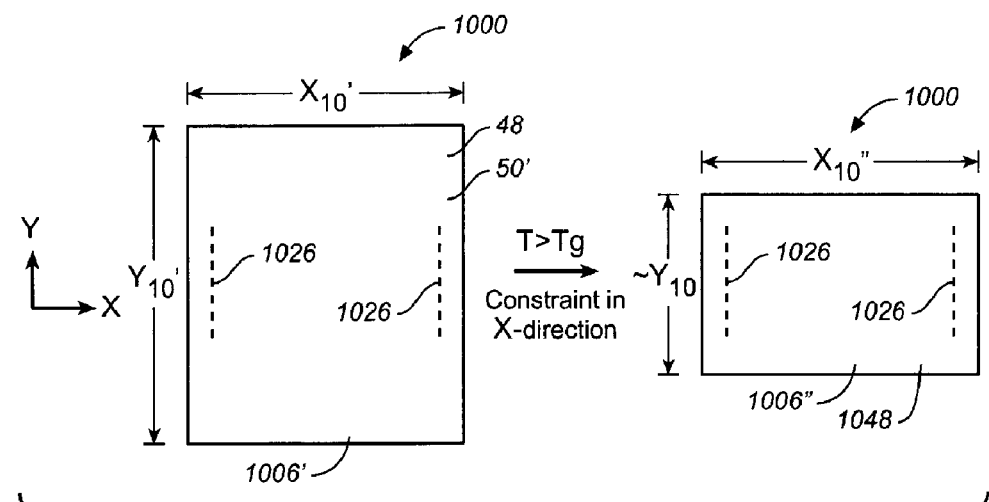
FIG. 10C shows the recovery of the strained configuration of the device or bandage illustrated in FIG. 10A in the presence of a constraint in one direction.

A variation of a bandage or device for ameliorating scar and/or keloid formation is shown in FIGS. 10A-C. As illustrated in FIG. 10A, a device or bandage 1000 includes a polymeric backing layer 1048 that has a first configuration 1006 that is approximately the shape of a planar rectangular sheet having width $X_{10}$ and length $Y_{10}$. First configuration 1006 has been stored into polymeric layer 1048, e.g., by crosslinking or by pre-stretching. The polymeric layer 1048 can be heated above the polymer $T_g$ and deformed, e.g., by applying force in both X- and Y-directions, to adopt a second configuration 1006'. Strained configuration 1006' can also have an approximately planar rectangular sheet conformation, but with width $X_{10}'$ and length $Y_{10}'$. Second configuration 1006' can be stabilized, e.g., by subsequently cooling the polymeric layer 1048 to a temperature below $T_g$ while still under strain. Strain can then be removed, and strained configuration 1006' can be stable if held at a temperature sufficiently below the polymer $T_g$, e.g., about 10° C., about 15° C., about 20° C., or more, below the polymer $T_g$. Upon reheating device or bandage 1000 to a temperature above $T_g$ in the absence of significant constraint, the stabilized strained configuration 1006' may generally recover its initial configuration 1006 with a width of approximately $X_{10}$ and a length of approximately $Y_{10}$, as illustrated in FIG. 10B.

The devices or bandages described here are typically removably secured to a skin surface while in a strained configuration. If a bandage or device in its strained stabilized configuration experiences a load or constraint as it is reheated above $T_g$, its ability to recover to its initial configuration may be limited by that constraint. Referring to FIG. 10C, strained configuration 1006' is removably secured to skin (not shown) via securing mechanisms 1026 and is therefore subject to constraint. Strained configuration 1006' recovers to a third configuration 1006'' instead of initial configuration 1006. In the variation illustrated in FIG. 10C, device 1000 is constrained primarily in the X-direction only. Device 1000 can reach third configuration 1006'' that has recovered its initial length $Y_{10}$ to a substantial degree, but has recovered its width only partially along the X-direction, resulting in a recovered X-direction $X_{10}''$ that is between $X_{10}'$ and $X_{10}$.

When the devices or bandages are made from a polymer, the polymer may be of any suitable thickness. For example, the polymer thickness may be from about 100 or 200 microns to a few millimeters. The thickness of polymer sheets, e.g., silicone polymer sheets or shape memory polymer sheets, can be selected to provide the devices or bandages with sufficient load carrying capacity to achieve desired recoverable strains, and to prevent undesired amounts of creep deformation of the bandages or devices over time. In some variations, the thickness across devices or bandages is not uniform, e.g., the thickness across the device can be varied to change the stiffness, the load carrying capacity, or recovery strains in selected orientations and/or locations. In some variations, the devices or bandages are tapered near the edges to reduce thickness. Devices or bandages having tapered edges may increase the flexibility of the devices or reduce the likelihood that the devices or bandages can debond over time. In addition, devices with tapered edges may have increased comfort for the wearer.

In some variations, the bandages or devices comprise a mesh or wire frame. As illustrated in FIG. 11, elements 1160, 1162 forming at least part of mesh or frame 1130 can be incorporated into bandage or device 1100. In some variations, elements 1160, 1162 comprise a shape memory metal. That is, in some variations, the bandages or devices comprise a shape memory metal formed as a mesh or wire frame. In other variations, elements 1160, 1162 comprise shape memory polymers. In still other variations, elements 1160 or elements 1162 can be elastic fibers having a first tensile stressed configuration (not shown). Device 1100 can be removably secured to skin in the proximity of a wound site with elements 1160 or 1162 in their tensile stressed configuration. Although FIG. 11 depicts the mesh or frame 1130 having a lattice configuration with elements 1160 oriented approximately perpendicular to elements 1162, the elements 1160, 1162 may have any suitable configuration, e.g., linear stripes, diagonals, circles, ovals, or various three-dimensional configurations such as a three-dimensional mesh. When elements 1160, 1162 are shape memory metals, any suitable shape memory metal may be used, e.g., nickel titanium alloys and the like. The elements 1160, 1162 of the devices or bandages may also include polymers in addition to shape memory metals.

If a shape memory metal is used, the first unstrained configuration may be formed by shaping the metal in its high strength austenitic phase to a desired configuration. The second strained configuration may be stored by first plastically deforming the shape memory metal while the metal is heated above $M_f$, the temperature at which the metal fully adopts its soft martensic phase, and then cooling the metal while still under strain to a temperature below $A_f$, the temperature at which the metal recovers its high strength austenitic phase. If the strained second configuration of shape memory metal is heated above $M_f$ while not constrained, the shape memory metal can recover to essentially the dimensions of the first configuration. If the strained second configuration of the shape memory metal is heated above $M_f$ while constrained, it may recover only partially to the dimensions of the first configuration, i.e., it will recover to a third configuration. In some variations, the shape memory metal may be a wire, mesh, or foil, e.g., a thin wire, a thin mesh, or a thin foil. Any combination of wire, mesh, or foil shape memory metals may also be used. Of course, combinations of different shape memory materials, e.g., more than one shape memory metal or a shape memory metal and a shape memory polymer, may be used in devices or bandages. In still other variations, shape memory metals are covered at least partially with plastic or fibers, either while in their first unstrained configuration or in their second strained configuration. The phase transition temperature of shape memory metals used in bandages or devices described herein may be chosen to be compatible with use on skin, e.g., between about 35° C. and about 55° C. In some variations, the devices may include one or more thermally insulating layers that can allow the use of shape memory metals having transition temperatures higher than about 55° C. In some variations, body heat can be sufficient to increase the temperature of shape memory metals used in the devices above $M_f$.

In addition to those variations described above with respect to FIGS. 10A-C, variations of first unstrained configurations, second strained configurations, and third recovered configurations are illustrated in FIGS. 12A-D, 13A-D and 14A-D. FIG. 12A shows a first configuration 1206 of a device 1200 having a rectangular shape with width $X_{12}$ and length $Y_{12}$. Device 1200 is heated above a transition temperature, e.g. $T>T_g$ or $T>M_f$, to adopt a strained second configuration 1206'. Strained second configuration 1206' is stabilized by cooling device 1200 below its transition temperature. In this variation, strained configuration 1206' is strained relative to initial configuration 1206 primarily by expansion along the Y-direction and is substantially unstrained in the X-direction, having width $X_{12}$ and length $Y_{12}'$ (FIG. 12B). At a temperature below the transition temperature, strained configuration 1206' is applied proximate the wound 120 and removably secured to the skin (not shown) via securing mechanisms 1226 proximate the device edges 1253 (FIG. 12C). Heat is applied to strained configuration 1206' such that its temperature exceeds its transition temperature and it will attempt to adopt its original first configuration 1206. However, because configuration 1206' is constrained along the Y-direction by having been attached to skin along two edges 1253 in its deformed state, the device 1200 may not recover its original Y-direction $Y_{12}$. Instead, the device may recover to an intermediate third configuration 1206" (FIG. 12D) having length $Y_{12}"$, where $Y_{12}"$ is a length between the original length $Y_{12}$ of the first configuration 1206 and strained length $Y_{12}'$ of strained configuration 1206'. The secured configuration 1206" transfers stress along direction Y to the skin at and external to the securing mechanisms 1226, indicated by arrows 1252. Therefore, device 1200 attached in configuration 1206" can shield, i.e., unload, wound 120 from endogenous and/or exogenous stress in at least direction Y, thereby ameliorating scar formation at wound 120.

Figure 13A:
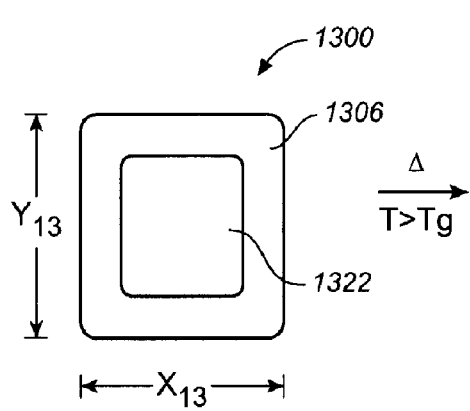
FIGS. 13A-D illustrate a device or bandage having a first configuration, a strained second configuration attached to skin, and a third configuration attached to skin. The third configuration differs from the second configuration in two directions.
Figure 13B:
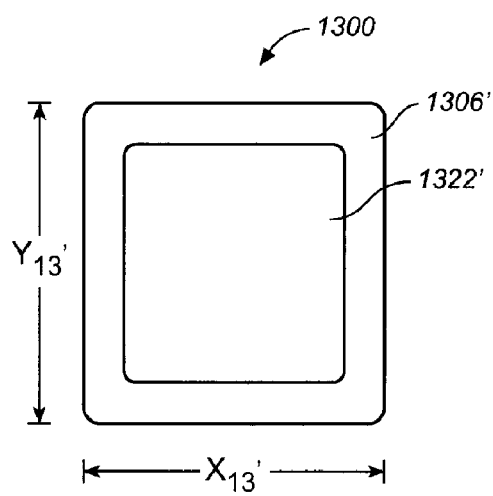
Figure 13C:
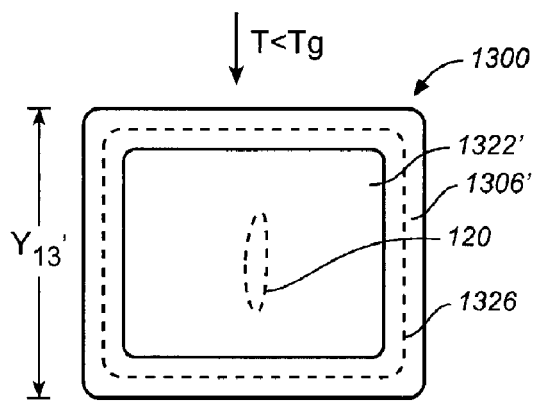
Figure 13D:
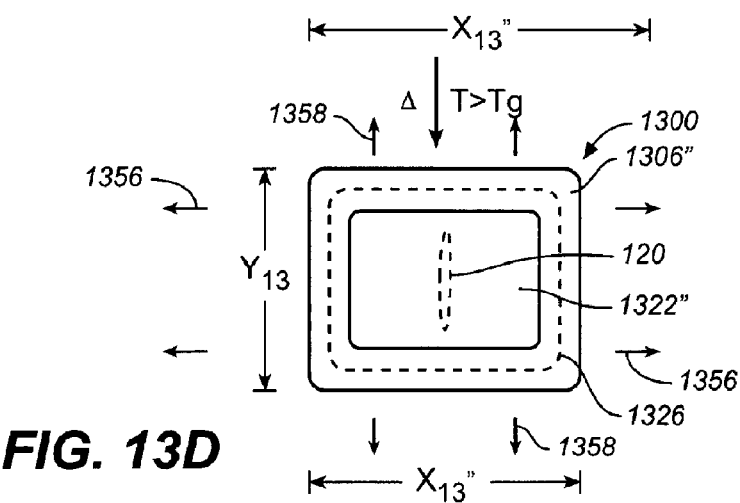

FIG. 13A illustrates a variation of a device 1300 having a first configuration 1306. First configuration 1306 is approximately rectangular with width $X_{13}$ and length $Y_{13}$ and includes aperture 1322. The device is heated above its transition temperature, e.g., $T_g$ or $M_f$, and strained in both X- and Y-directions. As illustrated in FIG. 13B, device 1300 in strained configuration 1306' is also approximately rectangular with width $X_{13}'$ and length $Y_{13}'$. In some variations, the size and/or shape of aperture 1322 can change to form aperture 1322' in strained configuration 1306'. Device 1300 is stabilized in strained configuration 1306' by cooling below its transition temperature while still under strain. As shown in FIG. 13C, device 1300 in its deformed configuration 1306' is removably secured to the skin surface via securing mechanism 1326 to frame wound 120. Although securing mechanism 1326 is illustrated as approximately following the shape of device 1300, other variations may be used as well. For example, the device can be removably secured to the skin at spaced apart securing sites, or removably secured to the skin around the periphery of the device. After device 1300 is secured to skin, heat is applied to increase the temperature of the device above its transition temperature so that the device will attempt to recover to its original configuration 1306. If device 1300 in strained configuration 1306' is subject to constraint, e.g., because it is secured to the skin, it may not be able to recover fully to initial configuration 1306 and instead may reach a third configuration 1306". Third configuration 1306" can be intermediate between first configuration 1306 and second configuration 1306', having width $X_{13}"$ between $X_{13}$ and $X_{13}'$ and length $Y_{13}"$ between $Y_{13}$ and $Y_{13}'$. As indicated by arrows 1356 and 1358, device 1300 can shield, i.e., unload, wound 120 from endogenous and/or exogenous stress in at least two directions, thereby ameliorating scar formation at wound 120.

Another variation of a device or bandage is illustrated in FIGS. 14A-D. As shown in FIG. 14A, device 1400 has a first configuration 1406 that is approximately circular or oval having cross-sectional diameters $D_1$ and $D_2$. Device 1400 is strained while heated above its transition temperature to form second configuration 1406' (FIG. 14B). In this variation, device 1400 is strained in both X- and Y-directions resulting in a circular or oval second configuration 1406' with cross-sectional diameters $D_1'$ and $D_2'$. The temperature of device 1400 is then lowered below the transition temperature while device 1400 is still under strain so that strained configuration 1406' is stable. Device 1400 is removably secured to skin (not shown) with securing mechanisms 1426 over wound 120 while in deformed configuration 1206' (FIG. 14C). Although securing mechanism 1426 are shown here as sutures, staples, microneedles, or anchors, or the like device 1400 can be secured to the skin surface in any suitable fashion, as described above. Heat is applied to increase the temperature of device 1400 above its transition temperature, e.g., $T_g$ or $M_f$. Deformed state 1406' can then adopt its original configuration 1406, subject to constraint. As illustrated in FIG. 14D, if device 1400 experiences significant constraint in both X- and Y-directions, the resulting configuration 1406" can be approximately circular or oval with cross-sectional diameters $D_1"$ and $D_2"$, where $D_1"$ is approximately between $D_1$ and $D_1'$ and $D_2"$ is approximately between $D_2$ and $D_2'$. In some variations, the constraint in one or both directions will be small enough such that $D_1"$ is approximately equal to $D_1$ and/or $D_2"$ is approximately equal to $D_2$. In other variations, constraint in one direction will be greater than in another direction. In some variations, skin compliance constrains the recovery of strained configuration 1406'. Device 1400 may transfer stress from the wound site to skin at or external to securing mechanisms 1426, thereby shielding wound 120 from endogenous and/or exogenous stress and ameliorating scar formation. If either $D_1"$ or $D_2"$ is substantially changed from $D_1'$ or $D_2'$, respectively, then device 1400 can shield wound 120 from endogenous and/or exogenous stress in at least one direction. If both $D_1"$ and $D_2"$ are substantially different $D_1'$ and $D_2'$, respectively, device 1400 can protect wound 120 from endogenous and/or exogenous stress in at least two directions.

In some variations, the devices and bandages may comprise or be made out of more than one type of material, e.g., more than one type of polymer or more than one type of shape memory material. For example, a device can comprise two different silicone polymers or two different shape memory materials, e.g., two different shape memory polymers, two different shape memory metals, or a shape memory polymer and a shape memory metal. If more than one type of material is used in a device, the materials selected can have different transition temperatures, different amounts of strain that can be incorporated into a strained configuration, or different abilities to recover an initial configuration against constraint, i.e., different load carrying capacities when heated above a transition temperature.

Figure 15A:
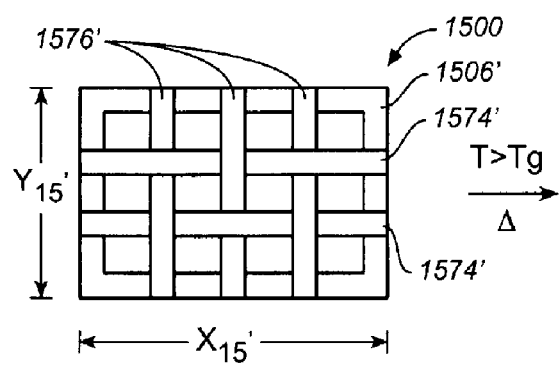
FIGS. 15A-B illustrate a device or bandage that can shield a wound from endogenous and/or exogenous stress preferentially in one direction.
Figure 15B:
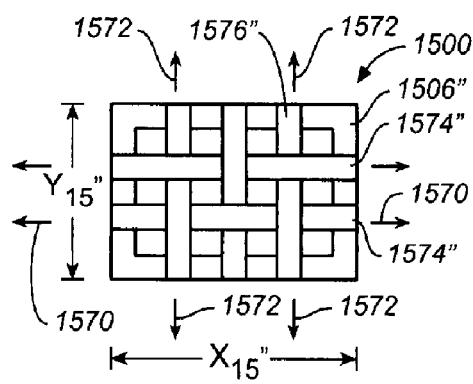

A variation of a device 1500 comprising two shape memory polymers is illustrated in FIG. 15A. Device 1500 forms a rectangle with width $X_{15}'$ and length $Y_{15}'$ in its stable, strained configuration 1506'. Device 1500 in its strained configuration 1506' comprises strained bands or fibers 1574' extending in the X-direction made of a first shape memory material and strained bands or fibers 1576' extending in the Y-direction made of a second shape memory material. Initial configuration (1506) is not shown. Although FIG. 15A depicts bands or fibers 1574, 1576' as being interwoven, they may or may not be interwoven. Device 1500 in second strained configuration 1506' is attached to skin (not shown). If device 1500 is heated above the transition temperature for both shape memory polymers, then differential recovery may occur in X- and Y-directions because of different relative strains or different compliances for the two materials. As illustrated in FIG. 15B, strained bands or fibers 1576' relax to state 1576" and strained bands or fibers 1574' relax to state 1574" to result in third configuration 1506" having width $X_{15}"$ and length $Y_{15}"$. In this variation, the percentage change between relaxed bands 1574" and strained bands 1574' is less than the percentage change between relaxed bands 1576" and strained bands 1576'. This asymmetry in turn leads to device 1500 in it's applied third configuration 1506" preferentially shielding, i.e., unloading, the wound (not shown) from endogenous and/or exogenous stress experienced in the X-direction, as indicated by arrows 1570 and 1572.

Figure 16A:
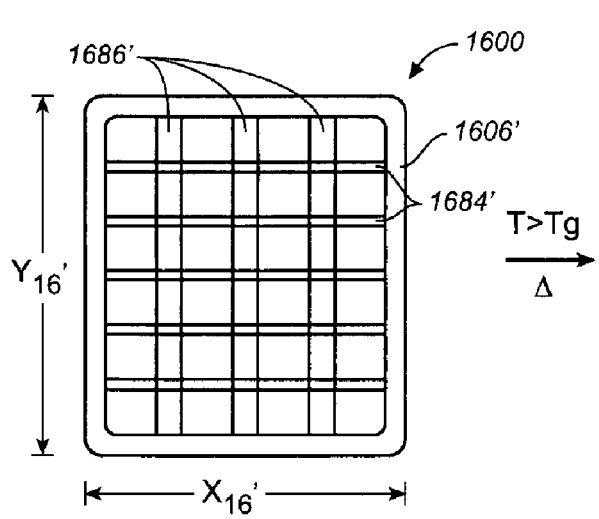
FIGS. 16A-B illustrate another variation of a device or bandage that can shield a wound from endogenous and/or exogenous stress preferentially in one direction.
Figure 16B:
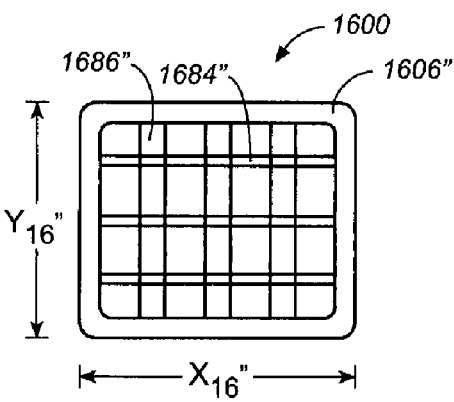

In some variations, devices can comprise elements having different dimensions to shield a wound preferentially in one or more directions from stress. As illustrated in FIG. 16A, a device 1600 in second strained stable configuration 1606' can be removably secured to skin in the proximity of a wound site. Device 1600 in second configuration 1606' has thick bands or fibers 1686' extending in the Y-direction and thin bands or fibers 1684' extending in the X-direction. Bands or fibers 1686' and 1684' may be made of the same or different materials, and may or may not be interwoven. If device 1600 is heated above the transition temperature for both elements 1686' and 1684', then third configuration 1606" in some variations can preferentially recover in the Y-direction because the recovered thicker bands 1686" in the Y-direction may have increased ability over the recovered thinner bands 1684" in the X-direction to overcome constraint resisting recovery to an initial configuration (not shown). That is, if a device 1600 is expanded in both X- and Y-directions in its strained second configuration 1606', then recovered third configuration 1606" can have the characteristic $Y_{16}"/Y_{16}' < X_{16}"/X_{16}'$.

Kits

Kits for ameliorating the formation of scars and/or keloids are also described here. In general, the kits comprise in packaged combination at least two devices, where each device is configured to be removably secured to a skin surface in proximity to a wound site. Each device shields, i.e., unloads, the wound from endogenous and/or exogenous stress.

In some variations, devices in a kit have different colors. Variations of kits can include devices that are color-coded for different scheduling regimes. For example, one color of a device may be provided for use at the beginning of the proliferative phase of wound healing and another color of a device may be provided for use at a later phase of wound healing. In some variations, devices in a kit have different shapes. For example, the shapes may be independently selected from the group consisting of rectangles, circles, squares, trapezoids, toroids, ovals, and segments and combinations thereof. In some variations, the devices in a kit may have different sizes or different thicknesses. The devices in a kit may also be configured to shield a wound from different amounts of endogenous and/or exogenous stress. Multiple devices in a kit may be designed to be applied in parallel, e.g., where more than one device is secured in proximity to the wound at the same time. Parallel application of devices encompasses scenarios in which the securing of the devices occurs at the same time, and in which a second device is secured while a first device remains secured. Multiple devices may also be applied in a serial fashion, where a first device is removed before a second device is secured. For example, some kits may include one device to be applied during an initial period such as the early part of the proliferative phase of wound healing, e.g., up to three days after injury, and then removed and a second device to be applied thereafter. Variations of kits may include an air blower, a heat gun, a heating pad, or the like, to raise the temperature of one or more devices. Some kits may contain at least one wound dressing, or at least one wound cleanser, or other components desirable or suitable for wound healing applications. The kits may also comprise instructions for using the devices and/or other components contained therein.

Methods

Methods for ameliorating the formation of scars and/or keloids are also described. The methods typically comprise applying a device configured to shield a wound from endogenous and/or exogenous stress in the proximity of the wound site. In some variations, the device is configured to shield the wound from both endogenous and exogenous stress.

The device may be applied during the proliferative phase of wound healing, which as described above, may be during the proliferative phase of wound healing after an old scar has been excised. The device may be applied and worn for any suitable length of time. For example, the device may be applied and worn for a period of at least about 10 days, at least about 20 days, at least about 30 days, at least about 40 days, at least about 50 days, at least about 60 days, at least about 70 days, at least about 80 days, at least about 90 days, at least about 100 days, and the like. In some variations, such as for wounds involving burns, the devices may be applied for a period over 100 days, e.g., for periods of about 6 months, about 9 months, about 12 months, or about 15 months, or even longer.

The devices are typically removed after a period of time, which may or may not be predetermined. For example, the period of time may be predetermined based on the type of wound. In other variations, the period of time may be actively monitored and therefore variable depending on the progress of the wound healing process.

The methods may also comprise applying to the skin in the proximity of a wound site, a second device configured to shield the wound from endogenous and/or exogenous stress. In other variations, the methods may comprise applying to the skin in the proximity of a wound site, a second device configured to be removably secured to a skin surface and to reduce wound stress in at least one direction. In some variations, the second device is configured to reduce wound stress in at least two directions. If a second device is applied, it may be applied in parallel manner with the first device. That is, the second device may be applied before the first device is removed. In some variations of the methods, the second device may be applied in a serial fashion, i.e., after the first device is removed. For example, a first device may be applied in an initial period such as the early part of the proliferative phase when tissue is swollen and wound exudates is high, and then removed. A second device can be applied thereafter, where the second device has been selected to have properties reflecting reduced swelling and/or wound exudates. In some variations of the methods, several devices may be applied in a parallel or serial fashion to reflect the wound environment as healing progresses.

EXAMPLES

Adult human wounds can exhibit extensive dermal scarring, whereas fetal human wounds and murine wounds typically do not. Young's modulus, the ratio of stress over strain, is a well-established measure of stiffness. Stiff materials, i.e., high modulus materials, exhibit small deformations (strain) in response to an applied force (stress). Soft or flexible materials have a low modulus and exhibit large deformations in response to applied force. The tension in a dermal layer depends on the resting tension of the skin, which can be affected by such factors as skin thickness, moisture content, and the extracellular matrix composition. Young's modulus of adult human skin is higher than that in murine adult or fetal skin. A murine model system for scarring in human dermal tissue can be created by inducing hypertrophic scarring on murine dorsal dermis by increasing mechanical forces on murine wounds to approximate those found in human wounds. Typical adult human skin is under about 0.4-1 N/mm² of stress while at rest. Healing adult human wounds are generally under about 0.6-2 N/mm² of stress.

Example 1

Demonstration that Stress can Induce or Promote Hypertrophic Scar Formation

Figure 17:
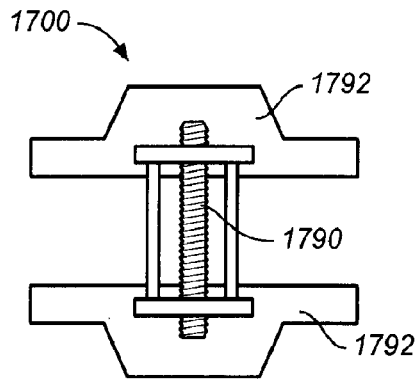
FIG. 17 illustrates a top view of a mechanical strain device used in Example 1 described below.

Four-week-old C5/BL6 mice were housed under standard protocols approved by the New York University Animal Care and Use Committee. Mechanical strain devices 1700 as illustrated schematically in FIG. 17 were constructed by securing 22 mm expansion screws 1790, available from Great Lakes Orthodontic Products, Tonawanda, N.Y., to titanium surgical Luhr plate supports 1792, available from Stryker-Leibinger Co., Freiburg, Germany. Expansion screws 1790 were secured to the plate supports 1792 using plastic interfaces and clear epoxy (not shown), available from Devcon Scientific, Riviera Beach, Fla., which was allowed to dry overnight. As illustrated schematically in FIGS. 18-19, two 2 cm linear full-thickness incisions (1802, 1802', 1902, 1902') were made 1.25 cm apart along the length of the dorsum (1810, 1910) of each mouse. The incisions were closed using 6-0 nylon sutures. On the fourth day following incision during the proliferative phase of wound healing, the sutures were removed.

Figure 18:
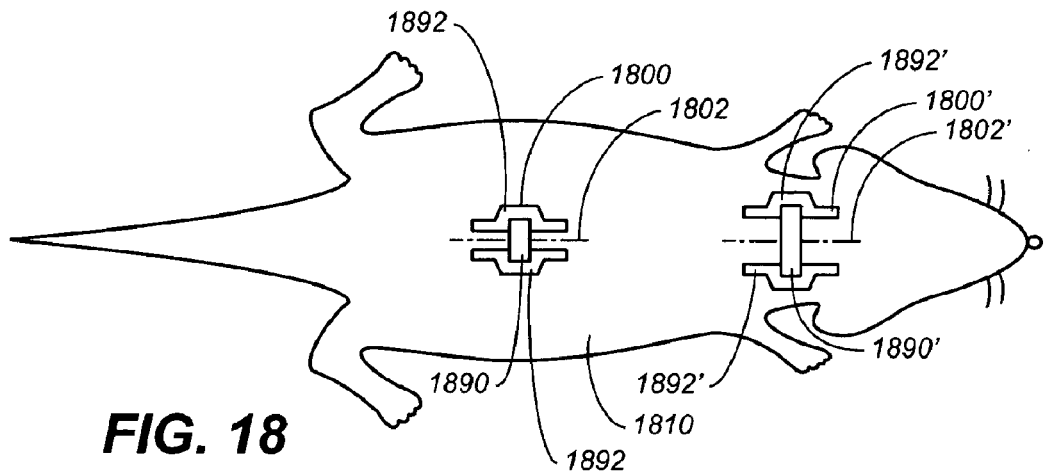
FIG. 18 illustrates the wound stress applied in murine models in Example 1, where the wounds were stressed in a direction approximately orthogonal to the incision direction.
Figure 19:
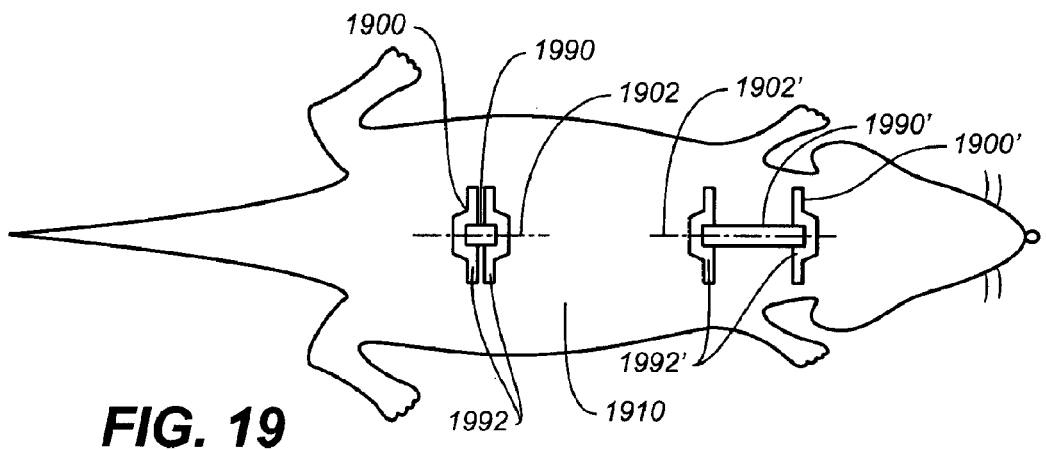
FIG. 19 illustrates the wound stress applied in murine models in Example 1, where the wounds were stressed in a direction approximately parallel to the incision direction.

As illustrated in FIG. 18, two mechanical strain devices 1800, 1800' were attached to a mouse's dorsum 1810 by suturing over wounds 1802, 1802', respectively. Strain devices 1800, 1800' did not physically contact wounds 1802 or 1802'. Strain devices 1800, 1800' were oriented relative to incisions 1802, 1802' to apply tension to the wounds in a direction approximately orthogonal to the incision direction. Analogously, as shown in FIG. 19, two strain devices 1900, 1900' were attached to a mouse's dorsum 1910 by suturing over wounds 1902, 1902', respectively. In this instance, strain devices 1900, 1900' were oriented relative to incisions 1902, 1902' to apply tension to the wounds in a direction approximately parallel to the incision direction. The strain devices 1800, 1900 were adjusted such that wounds 1802, 1902 experienced no additional strain. The strain devices 1800', 1900' were adjusted to apply tension to wounds 1802', 1902', respectively. On the fourth day following incision, approximately uniaxial tension on wounds 1802' was increased by expanding the distance between Luhr plates 1892' by 2 mm using expansion screw 1890', to generate an estimated stress of 1.5N/mm², and by 4 mm every second day thereafter for a total of 7 days to increase the applied stress to about 2.7N/mm². If tension was not increased mechanically using expansion screws 1890', natural elongation of the skin resulted in continuously decreasing force on the wounds. The range of applied stress (1.5 to 2.7 N/mm²) was chosen to replicate stress experienced by healing human wounds, and was below the breaking limit (9.6N/mm²) of murine wounds. A similar procedure was followed to apply stress to wounds 1902' by expanding the distance between Luhr plates 1992' using expansion screw 1990'. After 7 days, all tension was removed from the wounds. Scar tissue from stressed and unstressed wounds was collected once per week for one month, and again at six months post-incision. Three to six mice were used for each trial.

Tissue collected from unstressed wounds 1802, 1902 did not exhibit significant amounts of fibrosis after 3 weeks. However, tissue collected from wounds 1802' stressed in a direction approximately orthogonal to the incision direction as illustrated in FIG. 18 was characteristic of tissue from hypertrophic scars, having approximately 15 times greater cross-sectional areas than tissue from unstressed wounds. In addition, tissue collected from wounds 1902' stressed in a direction approximately parallel to the incision direction as illustrated in FIG. 19 was about 5 times greater in cross-sectional area than tissue collected from unstressed scars. The murine stressed scars displayed many characteristics of human hypertrophic scars. The murine stressed scars were raised, and demonstrated loss of rete pegs, adnexae and hair follicles. Stressed murine scars showed cellular hyperplasia, and fibroblasts oriented approximately parallel to collagen fibers and the direction of the strain. In addition, blood vessels in stressed wounds were approximately perpendicular to the wound. Stressed murine scars also showed collagen whorls, which are often observed in chronic human hypertrophic scars. Scar tissue from stressed murine wounds also demonstrated at least double cell density (cells per mm²) by Dapi nuclear staining. In addition, stressed murine scars averaged about 3 mm of height extending above the skin surface, but unstressed scars remained substantially flat.

After 11 days of tensile stress, total RNA was harvested from murine skin tissue and hybridized to Affymetrix 43K 2.0 GeneChips. The permutation-based algorithm Significance Analysis of Microarrays (SAM) showed 347 genes that were reproducibly distinguished in incisional wounds that had been subjected to tensile stress from incisional wounds that were not subjected to tensile stress (false discovery rate <0.05). Tensile stress on healing wounds induced expression of genes involved in extra cellular matrix formation, e.g., asporin, laminin B, procollagen or collagen types III-VII, lysyl oxidase, etc. Since human scars, hypertrophic scars and keloids are known to express excess matrix-associated proteins, these results can validate the murine model and indicate mechanical stress contributes to or causes human scar hypertrophy. In addition, genes related to angiogenesis (lysyl oxidase, VCAM-1, Angiopoietin-like 2 protein, RAMP2 or adrenomedullin receptor), multiple growth factors (IGF1, Bdnf, Osf2, Raf53, TFPI, Lef1, Csf3r), signal transducers (Vav, c-fes, creatine kinase, Ste20, Neki7, Dcamk1, Macs, Eif2ak3), and transcription factors (HIF-1a, c-maf, Tcf4, MITF4, Tert2ip, Mafb), which are all associated with cellular proliferation and differentiation, were induced by mechanical stress.

Figure 20:
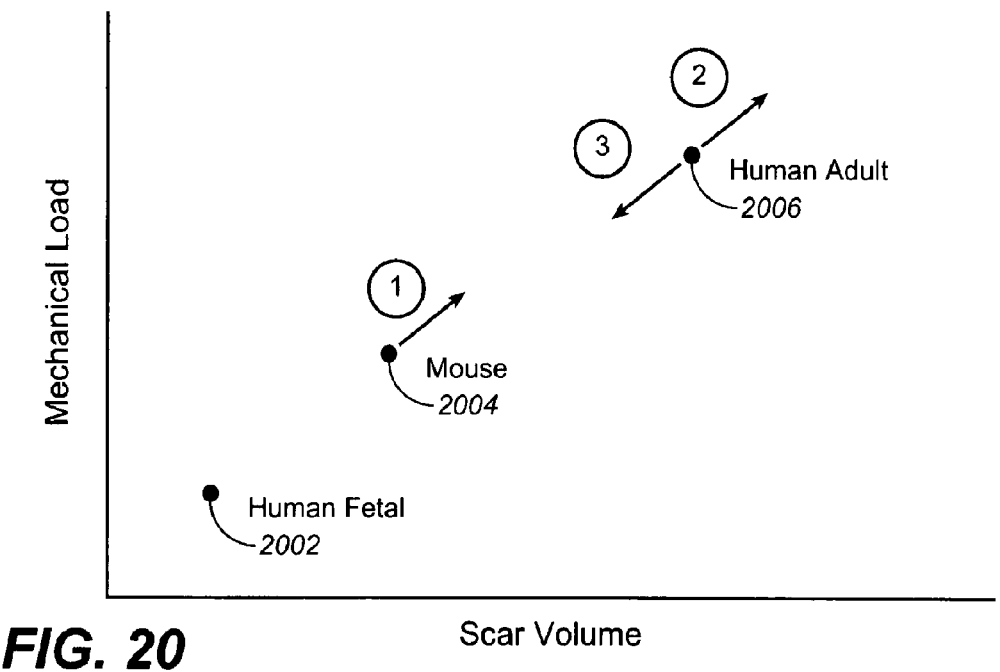
FIG. 20 illustrates a qualitative effect of mechanical load on scar volume.

FIG. 20 illustrates a qualitative effect of mechanical load on scar volume. Human fetal skin typically is almost completely relaxed and therefore under very low endogenous load. The dynamic resting tension as a measure of skin elasticity for human fetal skin is below the currently available limits of detection. Human fetal skin heals with little or no scar volume, as illustrated by point 2002. Murine skin is under a higher endogenous load, having a dynamic resting tension of about 0.06N/mm². The baseline scarring volume for murine skin is above that for human fetal skin, as indicated by point 2004. The data in this Example showed a positive correlation between mechanical load and scar volume for a murine model, as indicated by solid trend line 1 in FIG. 20. Adult human skin experiences an even higher endogenous load than murine skin, having a dynamic resting tension of 0.132N/mm². The resulting baseline scarring volume for human skin is higher than that of a mouse, and is indicated by point 2006. Thus, as indicated by dashed trend line 2, increased mechanical loading on a human adult wound may increase scar volume. Devices and methods described here can decrease both endogenous and exogenous loads on the wound region and are expected to decrease scar volume in humans, as indicated by dashed trend line 3. It should be understood that dashed trend lines 2 and 3 are prophetic, whereas solid trend line 1 indicates a qualitative correlation between mechanical load and scar volume observed for the murine model in this Example.

Example 2

Preparation of Exemplary Devices or Bandages

Polymer sheets of acrylate-based shape memory polymer Memori™ System with $T_g$ values of 20° C., 30° C. and 40° C., available from MedShape Solutions, Inc., 900 Anaconda Court, Castle Rock, Colo., were cut into rectangular, approximately planar, flexible bandages having in-plane dimensions of approximately 45 mm×20 mm. The sheets made of polymer having $T_g$ of 20° C. had thicknesses of approximately 200 microns and 500 microns. The sheets made of polymer having $T_g$ of 30° C. had a thickness of approximately 500 microns, and the sheets made of polymer with $T_g$ of 40° C. had a thickness of approximately 1000 microns. Each of a first set of 8 bandages was individually fixed between gripping fixtures and heated to about 60° C. to about 90° C. above $T_g$ for the polymer used in that bandage. The bandages were stretched along the longer dimension of the rectangle while heated above $T_g$ by translating the gripping fixtures apart at about 1 mm/minute to reach strains of about 8% to about 12%. Each bandage was cooled to well below $T_g$ for the polymer used in that bandage by inserting the straining stage with the bandage between the gripping fixtures into a freezer at −10° C. while the strains were imposed. After a cooling period of approximately one hour, each bandage was removed from the freezer and gripping fixtures and stored at laboratory ambient temperature of approximately 24° C., except for the bandages made from a polymer having $T_g$ of 20° C., which were kept in a refrigerator at approximately 5° C.

Subsequently, Duro-Tak 87-4287 pressure sensitive adhesive, available from National Starch and Chemical Company, Bridgewater, N.J., was applied to one side of the bandage. The pressure sensitive adhesive was in the form of an approximately 60 micron thick layer contained between two polymer release layers. One of the release layers was removed and the adhesive layer was then pressure applied to the polymer bandage using a hand roller to remove air bubbles at the interface between the adhesive and polymer. The excess adhesive layer was trimmed to the edges of the polymer bandage. The remaining release layer was then carefully removed. A wound dressing having approximate dimensions of 10 mm×5 mm obtained from commercially available bandages was affixed to the center of selected exemplary polymer bandages. A polymer release layer was subsequently reapplied over the adhesive and each bandage was stored at the storage temperatures noted above prior to use.

The polymer release layers were removed from selected bandages. Some bandages were heated approximately 20° C. to approximately 50° C. above $T_g$ for the polymer used in the respective bandages without being subject to constraint. When unconstrained, the bandages were generally observed to recover their approximate original unstrained size upon being heated above the polymer $T_g$. Other bandages made from polymers having $T_g$ of 30° C. were affixed to human skin in locations on the inside forearm using finger pressure. After affixing the bandages to skin, the bandages were heated above $T_g$ using a hot air blower. Temperatures were estimated to reach about 45° C. for a period of about 15 seconds. Partial recovery of the bandages was noted, achieving approximately 50% of the initially imposed strain. These results are summarized in Table 1 below.

TABLE 1

Strained bandage recovery with and without constraint

| Bandage Example | Polymer $T_g$ (° C.) | Polymer Thickness (microns) | Deformation T (° C.) | Strain (%) | Unconstrained Recovery (%) | Recovery after application to skin (%) |
|---|---|---|---|---|---|---|
| A | 20 | 200 | 80 | 8 | 100 | — |
| B | 20 | 200 | 90 | 12 | 100 | — |
| C | 20 | 500 | 80 | 8 | 100 | — |
| D | 20 | 500 | 90 | 12 | 100 | — |
| E | 30 | 500 | 90 | 12 | 100 | 50 |
| F | 30 | 500 | 120 | 12 | 100 | 50 |
| G | 40 | 1000 | 120 | 12 | 100 | — |

Example 3

Preparation of Exemplary Devices or Bandages

Polymer sheets of silicone MED 82-5010-05, MED 82-5010-10, and CSM82-4032-20 available from NUSIL TECHNOLOGY LLC, 1050 Cindy Lane, Carpinteria, Calif. 93013 USA, were cut into rectangular, approximately planar, flexible bandages having in-plane dimensions of approximately 50 mm×40 mm. The MED 82-5010-05 and MED 82-5010-10 sheets had a Durometer value of 50 and had thicknesses of approximately 120 microns and 230 microns, respectively. The CSM82-4032-20 sheet had a Durometer value of 30 and had a thickness of approximately 490 microns.

Additional polymer sheets of silicone HT6240 available from Stockwell Elastomerics, Inc., 4749 Tolbut St., Philadelphia, Pa. 19136, USA, were cut into rectangular, approximately planar, flexible bandages having in-plane dimensions of approximately 50 mm×40 mm. The HT6240 sheet had a Durometer value of 40 and had a thickness of approximately 500 microns.

Subsequently, MED1356 pressure sensitive adhesive, available from NUSIL TECHNOLOGY LLC, 1050 Cindy Lane, Carpinteria, Calif. 93013, USA, was applied to one side of the bandage. The pressure sensitive adhesive was in the form of a viscous liquid and was applied with a metal spatula to a layer thickness of approximately 60 microns directly on the silicone bandages. The solvents in the pressure sensitive adhesive layer were allowed to evaporate according to directions from the manufacturer for a period of 30 minutes at 25° C. in a laboratory air environment.

The MED1356 pressure sensitive adhesive is made by the manufacturer with a range of allowable polymer-to-resin ratios, molecular weights of the resin, and viscosity of the polymer. These determine important properties of the pressure sensitive adhesive including the release force in a T-peel test and the force in a blunt probe tack test. The manufacturer has allowable ranges of these values (approximately 125 kg/m to 286 kg/m for the force in a T-peel test). Our studies revealed that it was important to maintain high values of the release force and blunt tack probe test in order to prevent relaxation of the silicone bandage once applied to the skin. For Lot n° 36232 of the MED1356 the values reported by the manufacturer were release force in a T-peel of 285.73 kg/m, and blunt probe tack test value of 0.50 kg. This batch resulted in no relaxation of the silicone once applied to the skin for periods in excess of 3 days. On the other hand, Lot n° 39395 of the MED1356 had values reported by the manufacturer of release force in a T-peel of 125.01 kg/m, and blunt probe tack test value of 0.45 kg. kg/m. This pressure sensitive adhesive exhibited creep relaxation that resulted in complete relaxation of the initial silicone strains in the first 24 hours after application.

Figure 21:
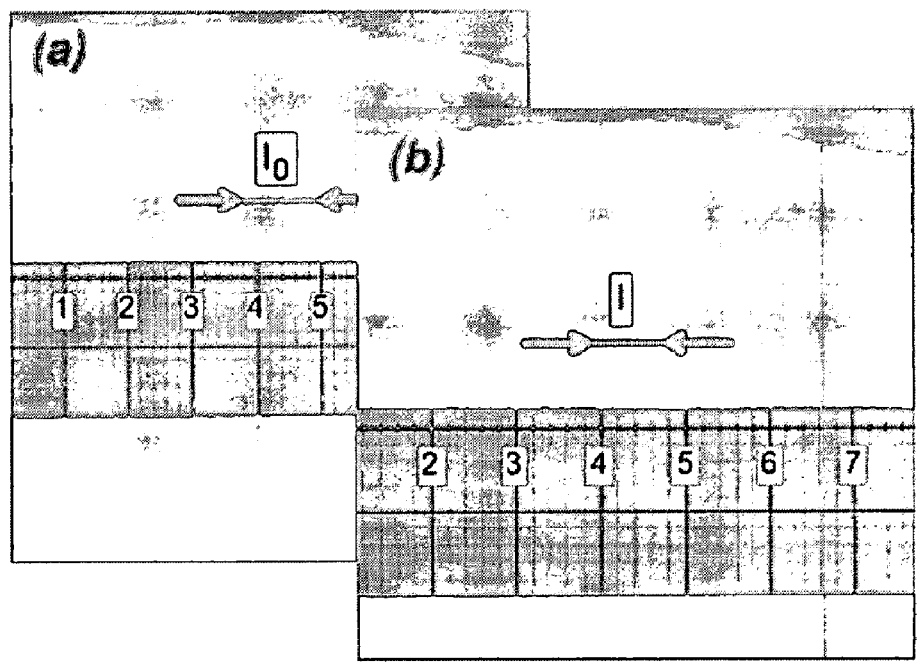
FIGS. 21A and 21B are optical micrographs showing the strains imposed on human forearm skin before an after (respectively) application of a device described herein.

Before application of the bandage, the skin was marked in the location where the bandage would be applied with parallel pen lines that were separated by approximately 10 mm. In some cases, orthogonal sets of lines were created. All of the silicone bandages employed were optically transparent and the lines were visible through the bandages after being affixed to the skin. This allowed the strains in the skin to be directly measured by measurement of the displacement of the lines before and after application of the bandage. By successive optical micrographs taken over a period of time the strains in the skin could be continually monitored. Optical micrographs showing initial pen lines on the skin (i.e., before application of the bandage), and after application of the bandage are shown in FIGS. 21A and 21B respectively. By measurement of the change in line separation, the strain imposed on the skin could be directly calculated.

The silicone bandages were initially stretched to predetermined engineering strains of 10%, 20%, 30%, 40%, 50% and 60% before being affixed to human skin in locations on the inside forearm. In some bandages the strains were imposed in only one orientation, and in others the strains were imposed biaxially in two orthogonal directions in the plane of the bandage. The strains were imposed by stretching the bandages and clamping them at the edges to an elastically stiffer polymer sheet using stiff paper clips. By varying the size of the stiffer polymer sheet, the initial strains in the bandage could be systematically varied.

After stretching the bandages to the predetermined strains, the bandages were allowed to relax for a period of approximately 10 min. This resulted in some stress relaxation in the bandage. The bandages were then affixed to human skin in locations on the inside forearm using finger pressure. After affixing the bandages to skin, the clamps were released and the bandages exhibited immediate elastic recovery. The extent of recovery strains depended on the initial strain in the bandage, the Durometer value and the thickness of the silicone polymer bandage. The final strain in the bandage and the strain imposed on the skin are determined by mechanical equilibrium involving both force and moment equilibrium being achieved between the bandage and the underlying skin.

Figure 22:
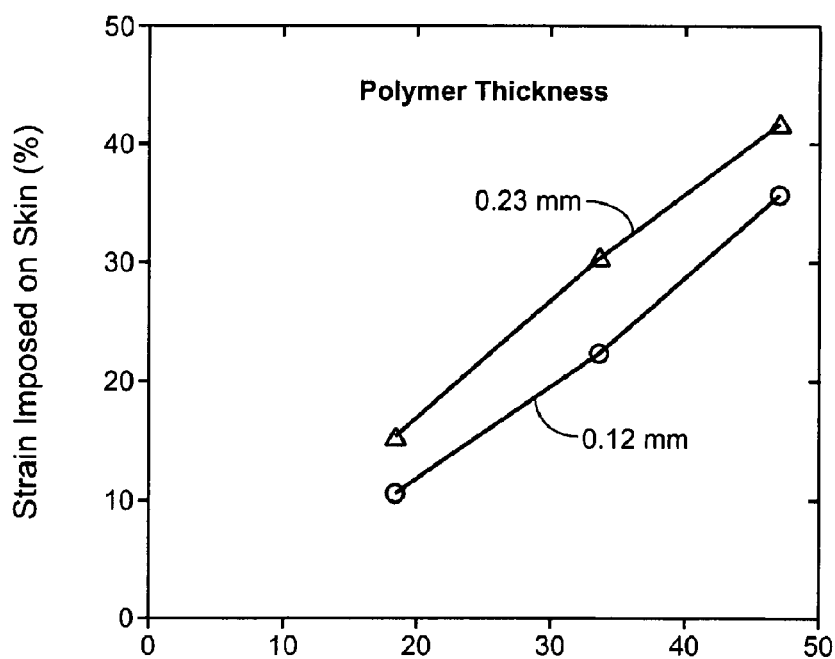
FIG. 22 is a graph showing strain imposed on the skin as a function of initial strain in the device backing.

The bi-directional strain and associated stress state in the skin under the affixed bandage could be systematically controlled by selection of the thickness, mechanical properties, and initial elastic strain of the silicone bandage. A set of curves of the initial tension strain in the device as a function of the resulting compressive strain in the skin was generated for different silicone polymer bandages having different polymer backing thicknesses. An example of the curves resulting from the MED 82-5010-05 and MED 82-5010-10 sheets which had Durometer values of 50 and polymer backing thicknesses of approximately 120 microns and 230 microns, respectively, is shown in FIG. 22.

Figure 23:
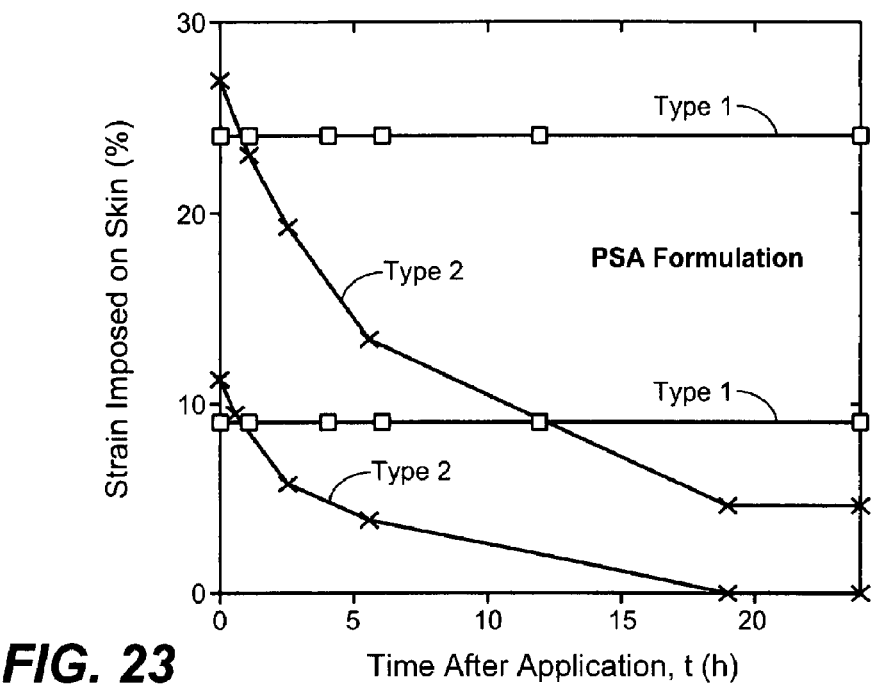
FIG. 23 is a graph showing strain imposed on the skin as a function of time, varying with pressure sensitive adhesive formulation.

FIG. 23 shows the effect of pressure sensitive adhesive formulation on skin strain imposed by the devices. The Type 1 formulation was that for Lot n° 36232 of the MED1356 with the higher values of release force in T-peel and blunt probe tack tests. This batch resulted in no observed relaxation of the silicone or skin strains once applied to skin for periods in excess of 3 days at two different strain levels. On the other hand, the Type 2 formulation was that of Lot n° 39395 of the MED1356, which had lower values of release force in T-peel and blunt probe tack tests. This pressure sensitive adhesive exhibited creep relaxation that resulted in almost complete relaxation of the initial silicone strains in the first 24 hours after application.

Figure 24:
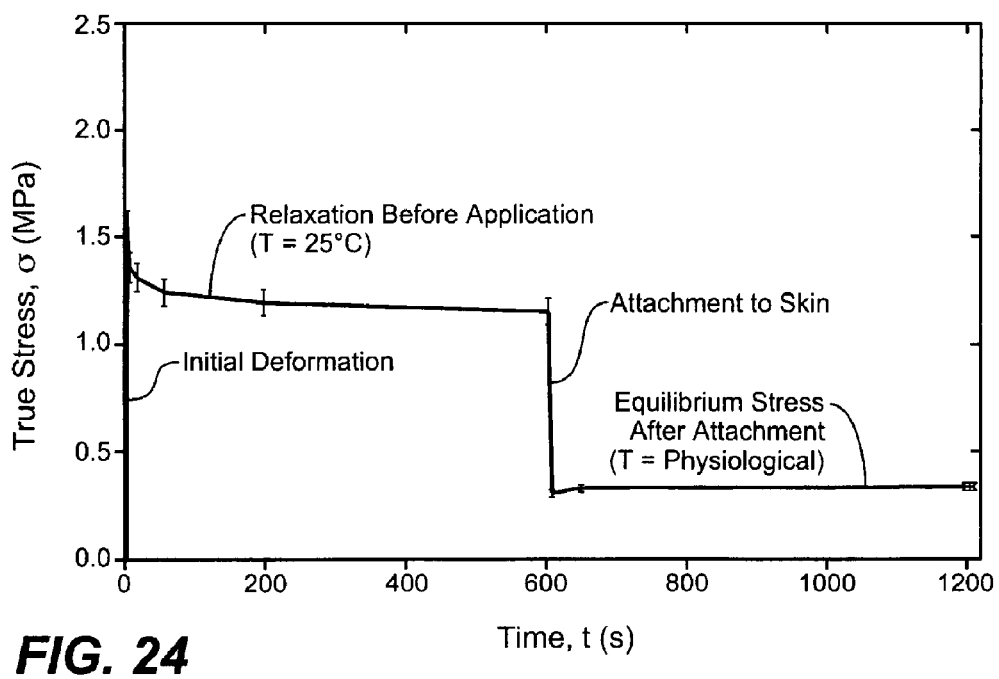
FIG. 24 depicts the extent of viscoelastic recovery during initial stages and subsequent stress after device attachment.

Even with the high levels of imposed strains examined, there was no report of discomfort or skin irritation for the periods studied. In order to achieve controlled strain states, the viscoelastic creep and recovery of the silicone bandages were assessed. This includes creep relaxation at room temperature associated with initial pre-straining of the bandage, followed by the elastic and viscoelastic recovery following device attachment to the skin. An example of the MED 82-5010 silicone, which has a Durometer value of 50 and a thickness of 120 microns, is shown in FIG. 24. Relaxation of the polymer bandage is clearly apparent following the initial straining at room temperature of 25° C. The relaxation begins to stabilize after approximately 10 minutes. Once the bandage is attached to skin there is an immediate elastic strain recovery. The final equilibrium stress and strain level is achieved and is stable with time as shown in FIG. 24. No further change in the skin or bandage strain was observed.

Figure 25:
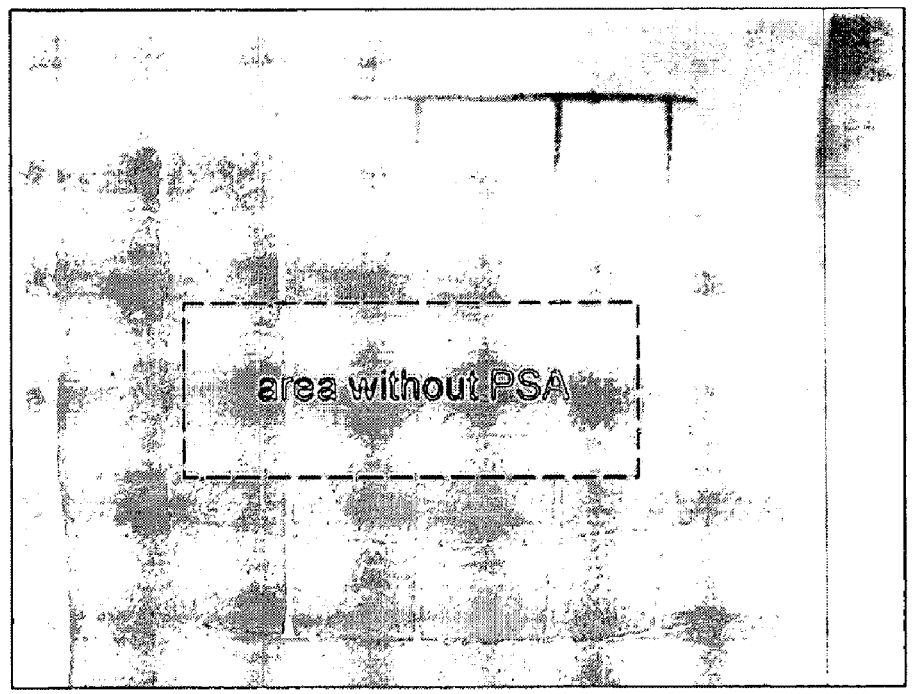
FIG. 25 is an optical micrograph showing a device attached to skin under stress having a pressure sensitive adhesive free region at its center.

We have further demonstrated that the mechanical strain and stress state of the wound region can be controlled underneath a region in the centre of the bandage that may be unbonded to the underlying skin and contain, for example, a wound dressing. This is shown in FIG. 25, which shows a polymer device with a central region approximately 35×20 mm in size that does not contain any adhesive layer bonding the device to the skin. Analysis of the underlying markings on the skin revealed the identical strains compared to the bonded regions (the curvature of the lines observed is associated with refraction through the transparent polymer layer in the presence of the air gap in the unbonded region).

While the inventive devices, bandages, kits and methods have been described in some detail by way of illustration and examples, such illustration and examples are for purposes of clarity of understanding only. It will be readily apparent to those of ordinary skill in the art in light of the teachings herein that certain changes and modifications may be made thereto without departing from the spirit and scope of the appended claims.

What we claimed is:

1. A method for treating a patient, comprising:
   maintaining tensile stress in a wound treatment device using an attachment device;
   adhering the wound treatment device to an epidermal skin surface surrounding a wound site using the attachment device; and
   relieving tensile stress in the wound treatment device by detaching the attachment device from at least a portion of the wound treatment device.

2. The method of claim 1, further comprising attaching the attachment device to the wound treatment device.

3. The method of claim 2, wherein attaching the attachment device to the wound treatment device comprises clamping the wound treatment device.

4. The method of claim 3, wherein clamping the wound treatment device comprises clamping at least one edge of the wound treatment device.

5. The method of claim 3, wherein clamping the wound treatment device comprises clamping the wound treatment device to an attachment device sheet.

6. The method of claim 2, wherein attaching the attachment device to the wound treatment device comprises clamping the wound treatment device to a polymer sheet having a greater stiffness than the stiffness of the wound treatment device.

7. The method of claim 6, further comprising varying the tensile stress in the wound treatment device by varying the polymer sheet.

8. The method of claim 1, further comprising sizing the wound treatment device to extend at least about 2 cm beyond the wound site along at least one dimension across the wound site.

9. The method of claim 8, wherein sizing the wound treatment device comprising cutting the wound treatment device from an unsized wound treatment device.

10. The method of claim 9, wherein the tensile stress maintained in the wound treatment device is at least about 60% relative to a relaxed state of the wound treatment device.

11. The method of claim 8, wherein sizing the wound treatment device comprises selecting the wound treatment device from a plurality of wound treatment devices.

12. The method of claim 1, further comprising relaxing tensile stress in the wound treatment device before applying the wound treatment device to the wound site.

13. The method of claim 12, wherein relaxing tensile stress in the wound treatment device lasts for at least 10 minutes.

14. The method of claim 12, further comprising re-exerting tensile stress on the wound treatment device after relaxing the tensile stress in the wound treatment device and before applying the wound treatment device to the wound site.

15. The method of claim 1, wherein detaching the attachment device from at least a portion of the wound treatment device comprises unclamping at least a portion of the attachment device from the wound treatment device.

16. The method of claim 15, wherein unclamping at least a portion of the attachment device from the wound treatment device comprises unclamping the attachment device from an edge of the wound treatment device.

17. The method of claim 1, wherein the tensile stress maintained in the wound treatment device is at least about 40% relative to a relaxed state of the wound treatment device.

18. The method of claim 17, wherein the tensile stress maintained in the wound treatment device is at least about 50% relative to a relaxed state of the wound treatment device.

19. The method of claim 1, wherein the wound treatment device is a pre-stressed wound treatment device.

20. The method of claim 1, further comprising sizing the wound treatment device to frame the wound site by at least about 2 cm.

21. The method of claim 1, further comprising sizing the wound treatment device to extend at least about 6 cm beyond the wound site along at least one dimension across the wound site.

22. The method of claim 1, further comprising sizing the wound treatment device to frame the perimeter of the wound site by at least about 6 cm.

23. The method of claim 1, further comprising sizing the wound treatment device to extend at least about 10 cm beyond the wound site along at least one dimension across the wound site.

24. The method of claim 1, further comprising sizing the wound treatment device to frame the perimeter of the wound site by at least about 10 cm.

25. The method of claim 1, wherein relieving tensile stress in the wound treatment device occurs after applying the wound treatment device to the wound site.

26. The method of claim 1, further comprising removing scar tissue from the wound site.

27. The method of claim 1, further comprising adjusting the directionality of the tensile stress.

28. The method of claim 1, further comprising adjusting the amount of the tensile stress.

29. The method of claim 1, wherein maintaining tensile stress in the wound treatment device comprises maintain biaxial tensile stress in the wound treatment device.

30. The method of claim 1, wherein relieving tensile stress in the wound treatment device comprises partially relieving tensile stress in the wound treatment device.

31. A method for treating a patient, comprising:
adhering a strained wound treatment device to an epidermal skin surface surrounding a wound site;
releasing at least some strain in the device after applying the device to the wound site;
manipulating a first tensile stress element to change the strain of the device after releasing at least some strain from the device.

32. The method of claim 31, further comprising changing the strain of the device using a second tensile stress element different from the first tensile stress element.

33. The method of claim 32, wherein the change in strain from the second tensile stress element is oriented in a different direction than the change in strain from the first tensile stress element.

34. The method of claim 32, wherein the second tensile stress element is configured to maintain at least some strain in the device while applying the device to the wound site.

35. A method for treating a patient, comprising:
maintaining an elastic wound treatment device in a strained configuration using an tensile stress element incorporated into the wound treatment device, wherein the tensile stress element is configured to resist recovery of the elastic wound treatment device to an unrestrained configuration;
adhering the wound treatment device in the strained configuration to an epidermal skin surface surrounding a wound site; and
manipulating the tensile stress element to relieve strain in the wound treatment device.

36. The method of claim 35, wherein the tensile stress element remains incorporated with the wound treatment device after manipulating the tensile stress element.

37. The method of claim 35, wherein manipulating the tensile stress element comprises heating the tensile stress element.

38. The method of claim 35, wherein manipulating the tensile stress element comprises releasing a spring element.

39. The method of claim 35, wherein manipulating the tensile stress element comprises applying a potential to a piezoelectric element.

* * * * *